United States Patent
Xu et al.

(10) Patent No.: US 6,512,102 B1
(45) Date of Patent: Jan. 28, 2003

(54) COMPOSITIONS AND METHODS OF DIAGNOSIS AND TREATMENT USING CASEIN KINASE I

(75) Inventors: Licen Xu, Fremont, CA (US); Stephen D. Harrison, Albany, CA (US); Lewis T. Williams, Mill Valley, CA (US)

(73) Assignee: Chiron Corporation, Emeryville, CA (US)

( * ) Notice: Subject to any disclaimer, the term of this patent is extended or adjusted under 35 U.S.C. 154(b) by 0 days.

(21) Appl. No.: 09/472,112

(22) Filed: Dec. 23, 1999

Related U.S. Application Data

(60) Provisional application No. 60/113,664, filed on Dec. 31, 1998.

(51) Int. Cl.$^7$ .............................................. C07H 21/04
(52) U.S. Cl. .................................... 536/23.2; 536/23.1
(58) Field of Search .............................. 536/23.1, 23.2; 435/193, 194, 7.721, 15, 91.1, 91.4, 320.1

(56) References Cited

U.S. PATENT DOCUMENTS

| | | | |
|---|---|---|---|
| 5,686,412 A | * 11/1997 | Hoekstra | ..................... 514/12 |
| 5,756,289 A | 5/1998 | Hoekstra | |

FOREIGN PATENT DOCUMENTS

| | | |
|---|---|---|
| EP | 0 608 876 A1 | 8/1994 |
| WO | WO 94/12530 | 6/1994 |
| WO | WO 95/19988 | 7/1995 |
| WO | WO 97/34013 | 9/1997 |
| WO | WO 99/02179 | 1/1999 |

OTHER PUBLICATIONS

Ngo et. al.; Computational Complexity, Protein Structure Prediction, and the Levinthal Paradox, 1994. In The Protein folding Problem and Teriary Structure Prediction (Merz, K. Jr. et al., eds), Birkhouser, Boston, pp. 491–494.*

Rudinger; Characteristics of the amino acids as components of a peptide hormone sequence, 1976. In Peptide Hormones (Parsons, J. A., ed.), University Park Press, Baltimore, pp. 1–5.*

Graves, Paul R. et al., Role of COOH–terminal Phosphorylartion in the Regulation of Casein Kinase Iδ*, The Journal of Biological Chemistry, (1995), pp. 21689–21694, vol. 290, No. 37.

Longenecker, K. et al., Three–Dimensional Structure of Mammalian Casein Kinase I: Molecular Basis for Phosphate Recognition, J. Mol. Biol. (1996), pp. 618–631, vol. 257.

Nakamura, T. et al., Axin, an Inhibitor of the Wnt Signalling Pathway, Interacts with β–catenin, GSK–3 β and APC and Reduces the β–catenin Level, Genes to Cells (1988) pp. 395–403, vol. 3.

Sakanaka, et al., Bridging of β–catenin and Glycogen Synthase Kinase–3 β by Axin and Inhibition of β–catenin–Mediated Transcription, Proc. Natl, Acad. Sci. (1998) pp. 3020–3023, vol. 95.

Matsumura et al., Phosphoprotein Kinases form Rat Liver Cytosol, Biochim, Biophys. Acta, 1972, pp. 237–241, vol. 289.

Rijsewijk et al., The Drosophila Homolog of the Mouse Mammary Oncogene int–1 is Identical to the Segment Polarity Gene wingless, Cell, Aug. 14, 1987, pp. 649–657, vol. 50, Cell Press.

Rowles et al., Purification of Casein Kinese I and Isolation of cDNAs Encoding Multiple Casein Kinase I–Like Enzymes, Proc. Natl. Acad. Sci. USA, Nov. 1991, pp. 9548–9552, vol. 88.

Nusse et al., Wnt Genes, Cell, Jun. 26, 1992, pp. 1073–1087, vol. 69.

Peifer et al., The Vertebrate Adhesive Junction Proteins β–Catein and Plakoglobin and the Drosophila Segment Polarity Gene Armadillo Form a Multigene Family with Similar Properties, The Journal of Cell Biology, Aug. 1992, pp. 681–691, vol. 118 (No. 3), The Rockefeller University Press.

Zhai et al., Recombinant Rabbit Muscle Casein Kinase I αIs Inhibited by Heparin and Activated by Polylysine, Biochemical and Biophysical Research Communications, Dec. 15, 1992, pp. 944–949, vol. 189 (No. 2), Academic Press, Inc.

Sutherland et al., Research Communication Inactivation of Glycogen Synthase Kinase–3β by Phosphorylation: New Kinase Connections in Insulin and Growth–Factor Signalling, Biochem J., 1993, pp. 15–19, vol. 296, Great Britain.

Graves et al., Molecular Cloning, Expression, and Characterization of a 49–Kilodalton Casein Kinase I Isoform from Rat Testis, The Journal of Biological Chemisty, Mar. 25, 1993, pp. 6394–6401, vol. 268 (No. 9), U.S.A.

Rubinfeld et al., Association of the APC Gene Product with β–Catenin, Science, Dec. 10, 1993, pp. 1731–1734, vol. 262.

Su et al., Association of the APC Tumor Suppressor Protein with Catenins, Science, Dec. 10, 1993, pp. 1734–1737, vol. 262.

(List continued on next page.)

Primary Examiner—Dave T. Nguyen
Assistant Examiner—Quang Nguyen
(74) Attorney, Agent, or Firm—W. Murray Spruill; Anne S. Dollard; Robert P. Blackburn

(57) ABSTRACT

The invention is generally directed to compositions and methods for affecting signal transduction using the casein kinase I (CKI) gene or gene product. The invention is more specifically directed to affecting the Wnt signal pathway using the CKI gene or gene product. The invention is particularly directed to using the CKI gene or gene product to treat and diagnose cancer, particularly breast and colon cancer. CKIε is the preferred species. The field of the invention is compositions and methods for modulating signal transduction using the (CKI) gene or gene products and variants thereof. The invention is more specifically directed to modulating the Wnt signal pathway using the CKI gene or gene product. The invention is particularly directed to using the CKI gene or gene product to treat and diagnose disorders mediated by the Wnt signal pathway, especially hyperproliferative disorders, particularly breast and colon cancer.

5 Claims, 10 Drawing Sheets

OTHER PUBLICATIONS

Weber–Hall et al., Developmental and Hormonal Regulation of Wnt Gene Expression in the Mouse Mammary Gland, *Differentiation*, 1994, pp. 205–214, vol. 57, Springer–Verlag.

Wong et al., Differential Transformation of Mammary Epithelial Cells by Wnt Genes, *Molecular and Cellular Biology*, Sep. 1994, pp. 6278–6286, vol. 14 (No. 9, American Society for Microbiology.

Sussman et al., Isolation and Characterization of a Mouse Homolog of the *Drosophila* Segment Polarity Gene *dishevelled*, *Developmental Biology*, 1994, pp. 73–86, vol. 166, Academic Press, Inc.

Fish et al., Isolation and Characterization of Human Casein Kinase Iε (CKI), A Novel Member of the CKI Gene Family, *The Journal of Biological Chemistry*, Jun. 23, 1995, pp. 14875–14883, vol. 270 (No. 25), The American Society for Biochemistry and Molecular Biology, Inc., USA.

Rubinfeld et al., Binding of GSK3β to the APC–β–Catenin Complex and Regulation of Complex Assembly, *Science*, May 17, 1996, pp. 1023–1026, vol. 272.

Molenaar et al., XTcf–3 Transcription Factor Mediates β–Catenin–Induced Axis Formation in Xenopus Embryos, *Cell*, Aug. 9, 1996, pp. 391–399, vol. 86.

Behrens et al., Functional Interaction of β–Catenin with the Transcription Factor LEF–1, *Nature*, Aug. 15, 1996, pp. 638–642, vol. 382.

Harland et al., Formation and Function of Spemann's Organizer, *Annu. Rev. Cell Dev. Biol.*, 1997, pp. 611–667, vol. 13.

Brunner et al., *Pangolin* Encodes a Lef–1 Homologue that Acts Dounstream of Armadillo to Transdue the Wingless Signal in *Drosophila*, *Nature*, Feb. 27, 1997, pp. 829–833, vol. 385.

Rubinfeld et al., Stabilization of β–Catenin by Genetic Defects in Melanoma Cell Lines, *Science*, Mar. 21, 1997, pp. 1790–1792, vol. 275.

Dale, Trevor C., Review Article Signal Transduction by the Wnt Family of Ligands, *Biochem J.*, 1998, pp. 209–223, vol. 329, Great Britain.

* cited by examiner

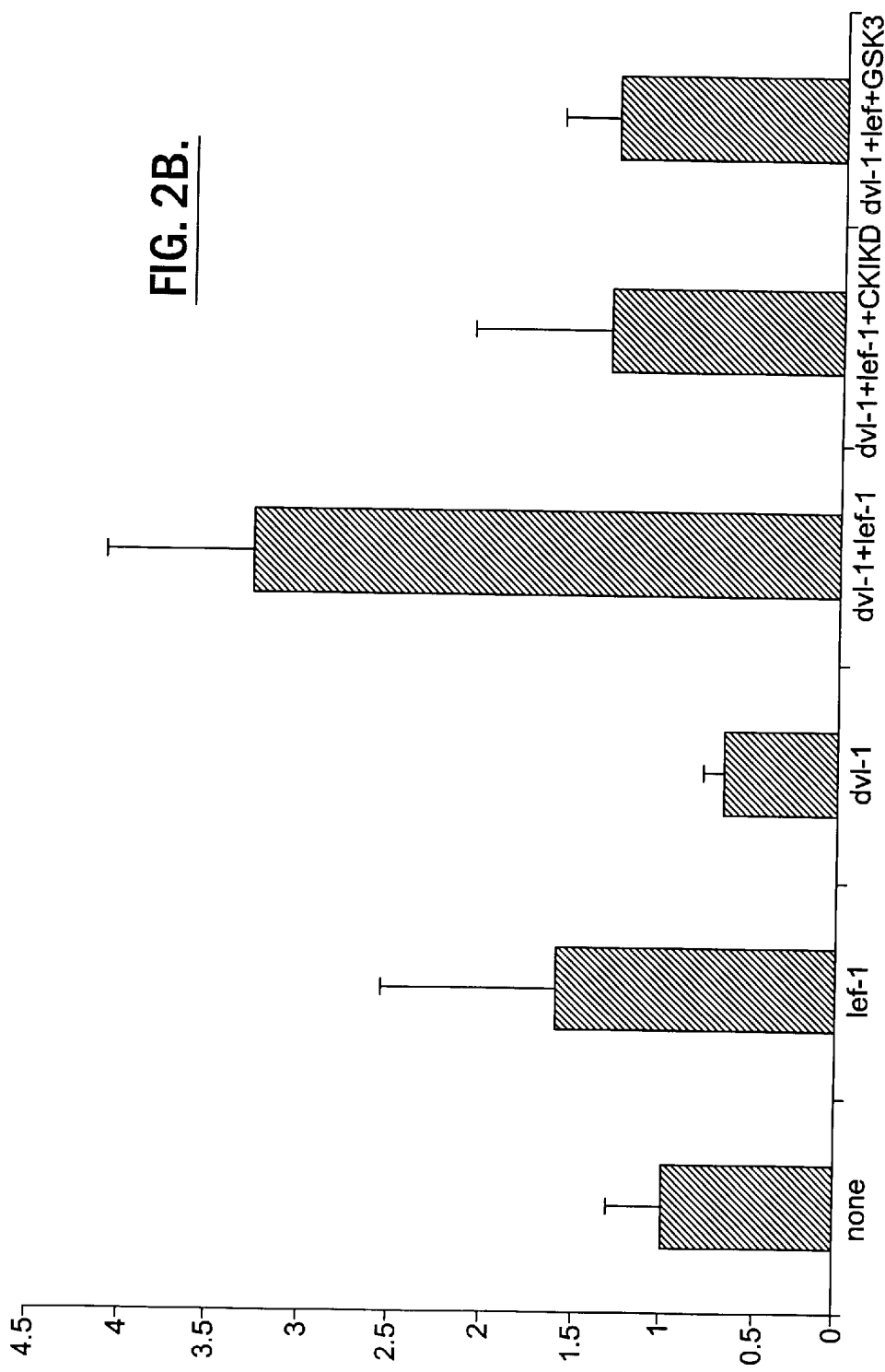

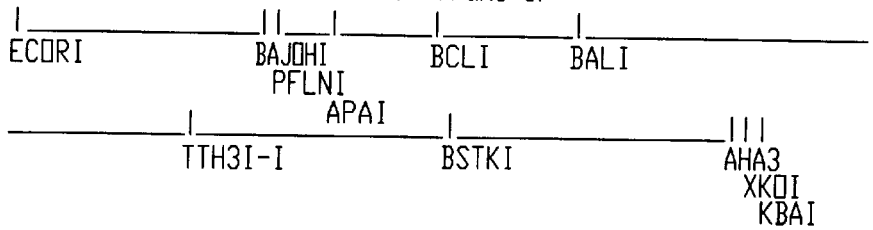

Argument Kap in DNA Strand P15.17_1.2.EcpRI-Xbal from the '/arp/lib/6mers/ file. Translation shown at frame 3.

```
|_____||__|_____|_____|_____
ECORI          BAJOHI   BCLI    BALI
               PFLNI
_____|_____APAI_|_____|||
TTH3I-I              BSTKI                        AHA3
                                                  XKOI
                                                  KBAI
```

```
                HetGluLeuArgValGlyAsoLysTyrArgLeuGlyArgLys
  3 ATTCGGCCACGAGGAAGCATGGAGTTGCGTGTGGGAAATAAGTATCGCCTGGGCCGAAAG
    TAAGCCCGTGCTCCTTCGTACCTCAACGCACACCCTTTATTCATAGCGGACCCGGCTTTC
  1 SCORI,

IleGlySerGlySerPheGlyAspIleTyrLeuGlyAlaAsnIleAlaSerGlyGluGlu
 63 ATCGGCAGTGGCTCCTTTGGAGACATCTACCTGGGTGCCAACATTGCCTCTGGTGAGGAA
    TAGCCGTCACCGAGGAAACCTCTGTAGATGGACCCACGGTTGTAACGGAGACCACTCCTT

ValAlaIleLysLeuGluCysValLysThrLysHiaProGlnLeuHieIleGluSerLys
133 GTAGCCATCAAGCTCGAATGTGTGAAGACGAAACATCCCCAGCTCCACATCGAGAGCAAG
    CATCGGTAGTTCGAGCTTACACACTTCTGCTTTGTAGGGGTCGAGGTGTAGCTCTCGTTC

PheTyrLysHetKetGlnGlyGlyValGlyLIeProSerIleLysTrpCysGlyAlaGlu
183 TTCTACAAGATGATGCAGGGCGGAGTGGGGATCCCGTCCATCAAGTCGTGCGGGGCTGAG
    AAGATGTTCTACTACGTCCCGCCTCACCCCTAGGGCAGGTAGTTCACCACGCCCCGACTC
    211 BAMHI, 220 PFLX1

GlyAspLlyAspValMatValNetGluLeuLeuGlyProSerLeuGluAspLeuPheAsn
213 GGAGACTATAACGTGATGGTCATGGAGCTGCTGGGGCCCAGCCTGGAGGACCTCTTCAAC
    CCTCTGATATTGCACTACCAGTACCTCGACGACCCCGGGTCGGACCTCCTGGAGAAGTTG
    276 APAI,

PheCysSerArgLysPheSerLeuLysThrValLeuLeuLeuAlaAspGlpMetIleSer
303 TTCTGTTCCCGGAAGTTCAGCCTCAAGACGGTGCTGTTGCTGGCCGACCAGATGATCAGC
    AAGACAAGGGCCTTCAAGTCGGAGTTCTGCCACGACAACGACCGGCTCGTCTACTAGTCG
    355 BCLI,

ArgIleGluTyrIleHisSerLysArnPheIleHisArgAspValLysProAspAsnPhe
363 CGCATCGAGTACATACACTCCAAGAACTTCATCCACCGGGATGTGAAGCCCGACAACTTC
    GCGTAGCTCATGTATGTGAGGTTCTTGAAGTAGGTGGCCCTACACTTCGGGCTGTTGAAG

LeuMetGlyLeuGlyLysLysGlyAsnLeuValTyrIleIleAspPheGlyLeuAlaLys
423 CTCATGGGCCTGGGGAAGAAAGGCAACCTGGTGTACATCATTGACTTCGGCCTGGCCAAG
    GAGTACCGGACCCCTTCTTTCCGTTGGACCACATGTAGTAACTGAAGCCGGACCGGTTC
    475 BALI,

LysTyrArgAspAlaArgThrHisGlnHisIIlsProTyrArgGluAsnLysAsnLeuThr
483 AAGTACCGCGATGCCCGCACACACCAGCATATTCCCTACCGGGAAAACAAGAACCTGACT
    TTCATGGCGCTACGGGCGTGTGTGGTCGTATAAGGGATGGCCCTTTTGTTCTTGGACTGA
```

FROM FIG. 3A.

```
        GlyThrAlaArgTyrAlaSerIleAsnThrHisLeuGlyIleGluGlnSerArgArgAsp
543  GGACTGCCCGCTATGCCTCTATCAACACCCACCTGGGCATTGAGCAAAGCCGTGGAGAT
     CCGTGACGGGCGATACGGAGATAGTTGTGGGTGGACCCGTAACTCGTAACTCGTTTCGGCAGCTCTA

AspLeuGluSerLeuGlyTyrValLeuMetTyrPheAsnLeuGlySerLeuPxoTrpGln
603  GACCTAGAGAGCTTGGGCTATGTGCTCATGTACTTCAACCTGGGCTCCCTGCCCTGCCCTGGCAG
     CTGGATCTCTCGAACCCGATACACGAGTACATGAAGTTGGACCCGAGGGACGGGACCGTC

GlyLeuLysAlaAlaThrLysArgGlnLysTyrGluArgIleSerGluLysLysMetSer
663  GGCCTCAAAGCAGCCACCAAGCGTCAGAAGTACGAGCGGATTAGCGAGAAGAAGATGTCA
     CCGGAGTTTCGTCGGTGGTTCGCAGTCTTCATGCTCGCCTAATCGCTCTTCTTCTACAGT

ThrProIleGluValLeuCysLysGlyTyrProSerGluPheSerThrTyrLeuAsnPhe
723  ACGCCAATCGAGGTCCTCTGCAAAGGCTACCCCTCCGAGTTCTCAACATACCTCAACTTC
     TGCGGTTAGCTCCAGGAGACGTTTCCGATGGGGAGGCTCAAGAGTTGTATGGAGTTGAAG

CysArgSerLeuArgPheAspAspLysProAspTyrSerTyrLeuArgGlnLeuPheArg
783  TGCCGCTCCCTGCGGTTCGATGATAAGCCTGACTACTCCTACCTGCGCCAGCTCTTCCGA
     ACGGCGAGGGACGCCAAGCTACTATTCGGACTGATGAGGATGGACGCGGTCGAGAAGGCT

AsnLeuPheHisArgGlnGlyPheSerTyrAspTyrValPheAspTrpAsnMetLeuLys
843  AATCTCTTTCACCCGCAGGGTTTCTCCTACGACTACGTCTTCGACTGGAACATGCTCAAA
     TTAGAGAAAGTGGGCCGTCCCAAAGAGGATGCTGATGCAGAAGCTGACCTTGTACGAGTTT

873 TTH3I,

PheGlyAlaAlaArgAsnProGluAspValAspArgGluArgArgGluHisGluArgGlu
903  TTCGGTGCAGCCCGGAATCCCGAGGATGTAGACCGGAAAGACGGGAGCACGAACGGGAA
     AAGCCACGTCGGGCCTTAGGGCTCCTACATCTGGCCCTTTCTGCCCTCGTGCTTGCCCTT

GluArgMetGlyGlnLeuArgGlySerAlaThrArgAlaLeuProProGlyProProThr
963  GAGAGGATGGGGCAGTTGCGAGGGTCCGCGACCAGAGCCCTGCCCCCTGGCCCCACCTACA
     CTCTCCTACCCCGTCAACGCTCCCAGGCGCTGGTCCTCCGGATTGGGGGACCGGGTGGATGT

GlyAlaThrAlaAsnArgLeuArgSerAlaAlaGluProValAlaSerThrProAlaSer
1093 GGGGCTACCGCCAACCGACTCCGAAGTGCAGCCGAGCCTGTGGCTTCCACTCCAGCCTCC
     CCCCGGATGGCGGTTGGCTGAGGCTTCACGTCGGCTCGGACACGGAAGGTGAGGTCGGAGG

ArgIleGlnGlnThrGlyAsnThrSerProArgAlaIleSerArgAlaAspArgGluArg
1083 CGCATCCAACAAACTGGCAATACTTCTCCCAGAGCGATCTCACGGGCCGACCGAGAGAGG
     GCGTAGGTTGTTTGACGGTTATGAAGAGGGTCTCGCTAGAGTGCCCGGCTGGCTCTCTCC

1088 BSTXI,

LysValSerMetArgLeuHisArgGlyAlaProAlaAsnValSerSerSerAspLeuThr
1143 AAGGTGAGCATGAGACTCCACAGAGGTGCCCCTGCCAATGTCTCCTCCTCAGACCTCACT
     TTCCACTCGTACTCTGAGGTGTCTCCACGGGGACGGTTACAGAGGAGGAGTCTGGAGTGA

GlyArgGlnGluValSerArgLeuAlaAlaSerGlnThrSerValProPheAspHisLeu
1203 GGGCGGCAAGAGGTCTCCGGGCTTGCAGCCTCACAGACAAGCGTGCCATTTGACCATCTT
     CCCGCCGTTCTCCAGAGGCCCGAACGTCGGAGTGTCTGTTCGCACGGTAAACTGGTAGAA
```

FROM FIG. 3B.

```
       GlyLysOP
1263   GGGAAATGAGGAGAGCGACCACAGACCAGTGTTTGCTTAGTGTCTTCACTGCATTTTCTT
       CCCTTTACTCCTCTCGCTGGTGTCTGGTCACAAACGAATCACAGAAGTGACGTAAAAGAA

1321 AHA3,

1323   TAAAAAAAAAAAAAAAAAAAACTCGAGCCTCTAGA
       ATTTTTTTTTTTTTTTTTTTTGAGCTCGGAGATCT

1342 XHOI, 1350 XBAI,
```

COMPOSITIONS AND METHODS OF DIAGNOSIS AND TREATMENT USING CASEIN KINASE I

CROSS-REFERENCE

This application claims the benefit of U.S. Provisional Application No. 60/113,664, filed Dec. 31, 1998.

FIELD OF THE INVENTION

The field of the invention is modulation of signal transduction using casein kinase I, polynucleotides encoding casein kinase I (CKI), and variants and fragments of CKI or the polynucleotides. The invention is specifically directed to modulating the Wnt pathway using CKI polypeptides or polynucleotides. The invention is particularly directed to using CKI polypeptides or polynucleotides for diagnosis and treatment of disorders mediated by the Wnt signal pathway, especially hyperproliferative disorders, and particularly breast and colon cancer. The invention further relates to assays for screening drugs using the polypeptides and polynucleotides. The invention further relates to methods for producing the polypeptides or polynucleotides, especially by recombinant means. The invention finally relates to pharmaceutical compositions containing CKI polypeptides, polynucleotides, antibodies, variants, and fragments.

BACKGROUND OF THE INVENTION

CKI is a ubiquitous protein kinase that was first described as one of the two protein kinases responsible for the Ser/Thr protein kinase activity on acidic rather than basic polypeptides in total cell extracts (Matsumara, *Biochem. Biophys. Acta* 289:237–241, (1972)). Since then, CKI homologs have been identified in eukaryotes from yeast to human. Several isoforms are known. Most organisms contain more than one isoform. In vertebrates seven CKI isoforms have been reported ($\alpha$, $\beta$, $\gamma1$, $\gamma2$, $\gamma3$, $\delta$ and $\epsilon$). They range in size from 34 to 49 kDa (Fish et al., *J. Biol. Chem.* 270:14875–83 (1995); Graves et al., *J. Biol. Chem.* 268:6394–6401 (1993); Rowles et al., *Proc. Natl. Acad. Sci. USA* 88:9548–9552 (1991); Zhai et al., *Biochem. Biophys. Res. Comm.* 189:944–949 (1992)).

Wnt Signaling

Signaling proteins and the hierarchies in which they operate are highly conserved in evolution. This is particularly true of Wnt signaling.

The Wnt genes encode a large family of secreted polypeptides that mediate cell-cell communication in various developmental processes. Cell fate, morphogenesis, and mitogenesis can be affected by changes in Wnt expression. Signal transduction by the Wnt family of ligands has been recently reviewed (McMahon, *Trends in Genetics* 8:236–242 (1992); Nusse, et al *Cell.* 69:1073–1087 (1992); Dale, *Biochem. J.* 329:209–223 (1998)). Wnt signaling has also been addressed in relationship to the formation and function of Spemann's organizer (*Ann. Rev. Cell Dev. Biol.* 13:611–667 (1997)).

Drosophila gene wingless (wg) is the ortholog of the mouse Wnt-1 gene (Nusse et al., *Cell* 69:1073–1087 (1992); Rijsewijk et al., *Cell* 50:649–657 (1987)). Wg binds to its receptor frizzled on the signal receiving cell. This is believed to result in a signal that is transmitted through the disheveled (dsh) gene product (Klingensmith et al., *Genes Dev.* 8:118–130 (1994); Noordermeer et al., *Nature* 367:80–83 (1994); Theisen et al., *Development* 121:347–360 (1994)), ultimately resulting in regulation of the zeste white 3 (zw3) serine/threonine kinase (also known as shaggy (sgg)) (Bourouis et al., *EMBO J.* 9:2877–2884 (1990); Siegfried et al., *Nature* 367:76–80 (1994); Siegfried et al., *Cell* 71:1167–1179 (1992)). Zw3 in turn negatively regulates the protein levels of the armadillo (arm) gene product (Peifer et al., *Dev. Biol.* 166:543–556 (1994a); Peifer et al., *Development* 111:1029–1043 (1991); Peifer et al., *Development* 120:369–380 (1994b); Riggleman et al., *Cell* 63:549–560 (1990)). All of these proteins have vertebrate counterparts. The Dsh ortholog in Xenopus is referred to as Xdsh and in mouse as Dvl-1 (Sussman et al., *Dev. Biol.* 166:71–86 (1994)). The Sgg ortholog in mammals is GSK3 (Sutherland et al., *Biochem. J.* 296:15 (1993)). The Arm ortholog in mammals is $\beta$-catenin (Peifer et al., *J. Cell. Biol.* 118:681–691 (1992)). Recent biochemical studies indicate that the vertebrate HMG-domain proteins Lef-1 and Xtcf-3 can physically interact with $\beta$-catenin and then regulate transcription of target genes (Behrens et al., *Nature* 382:638-42 (1996); Molenaar et al., *Cell* 86:391–399 (1996)). Genetic studies indicate that pangolin (Pan), a Drosophila homolog of the mammalian Lef-1, binds to Arm protein in vivo (Brunner et al., *Nature* 385:829-33 (1997)). Recently, CKI was shown to associate with and phosphorylate Dsh in Drosophila (Willert et al., *EMBO J.* 16:3089–3096 (1997)).

Wnt binds to its receptor (a Frizzled ortholog; see below) on the cell surface. This activates Dvl-1 (Disheveled in Drosophila). Activation of disheveled inhibits GSK3 (Sgg in Drosophila) activity. Normally, GSK3 is active and phosphorylates $\beta$-catenin. Phosphorylated $\beta$-catenin is degraded. When GSK3 activity is inhibited, the unphosphorylated $\beta$-catenin level increases, the protein enters the nucleus, binds to Lef-1 and the binary complex activates the Lef-1 enhancer causing transcription of target genes.

The Wnt signaling pathway is involved in mammary tumor and colon cancer. Ectopically-expressed Wnt-1 in mammary epithelium can induce hyperplasia, presumably by interfering with hormone-regulated Wnt pathway of other Wnt family members (Weber-Hall et al., *Differentiation* 57:205–214 (1994); Wong et al., *Mol. Cell. Biol.* 14:6278–6286 (1994)). $\beta$-catenin, a component in the Wnt signal pathway, is found associated with adenomatous polyposis coli (APC) which is a familial predisposition to colon cancer (Rubinfeld et al., *Science* 262:1731–1734 (1993); Su et al., *Science* 262:1734–1737 (1993)), and the levels of free $\beta$-catenin is regulated by APC together with GSK3 (Rubinfeld et al., *Science* 272:1023-6 (1996)). $\beta$-catenin is identified as an accomplice in causing colon cancer and is strongly implicated in melanoma (Rubinfeld et al., *Science* 275:1790–1792 (1997)).

The Wnt-1 proto-oncogene was originally identified as a common integration site of mouse mammary tumor virus in independently isolated adenocarcinomas of mammary epithelial tissue (Nusse et al. *Cell.* 31:99–109 (1982)). Ectopic expression of the normally silent Wnt-1 locus results from the introduction of transcriptional enhancers contained in the mouse mammary tumor virus long terminal repeats (Nusse et al. *Nature* 307:131–136 (1984); Nusse et al. *Cell.* 31:99–109 (1982)). Formal proof of a causative role for Wnt-1 in mammary oncogenesis has come from experiments on gene transfer into mammary epithelial cell lines (Brown et al. *Cell* 46:1001–1009 (1986); Rijsewijk et al. *EMBO J.* 6:127–131 (1987)) and transgenic mice (Tsukamoto et al. *Cell* 55:619–625 (1988)).

Accordingly, there is a need in the art for agents that can be used to modulate the Wnt pathway and to detect disorders mediated by this pathway.

SUMMARY OF THE INVENTION

The invention is based on the inventor's discovery that CKI can modulate the Wnt pathway. The inventor has found that normally, CKI allows a basal level of transduction in the Wnt pathway, but under-expression of CKI or a CKI variant lacking kinase activity can down-regulate the pathway, and over-expression of CKI can upregulate the pathway. A CKI variant causing over-phosphorylation should increase Wnt signal transduction. Increased signal transduction can result in a Wnt signal transduction mediated disorder, and particularly a hyperproliferative disorder. Hence, CKI or its variants or fragments can be used to modulate the Wnt pathway.

The invention encompasses the entire genus of CKI as well all species that retain the ability to affect Wnt signaling. These include homologs and orthologs from other animals or tissues as well as all isoforms.

The invention therefore provides a pharmaceutical composition comprising The invention also provides a pharmaceutical composition containing nucleic acid molecules encoding CKI.

The invention also provides variant CKI polypeptides containing a mutation in the kinase region that results in over- or under-phosphorylation of the CKI or its substrate.

The invention also provides variant CKI nucleic acid sequences containing a mutation in the kinase region that results in over- or under-phosphorylation of the CKI or its substrate.

In preferred embodiments, the CKI variant exhibits lower kinase activity than the wild-type CKI. Preferred variants contain less than approximately 50% of the activity.

In other preferred embodiments, the CKI variant has a lower capability of being phosphorylated than the wild-type CKI. In preferred embodiments, the variant CKI has less than 50% of the capability of being phosphorylated.

A specific disclosed embodiment is shown in SEQ ID NO:1, but in which amino acid 38 contains a substitution of arginine for lysine in the kinase domain (amino acids 1–69).

The invention is also directed to a CKI variant having a C-terminal deletion in the area homologous to 304-end in SEQ ID NO:1.

The invention also provides fragments of the CKI polypeptides and variants, particularly fragments containing the kinase region.

The invention also provides fragments of the CKI nucleic acid sequence and variants, particularly fragments containing the kinase region.

The invention also provides antisense nucleic acid molecules that bind to the coding strand of CKI nucleic acid molecules, particularly the kinase region.

The invention also provides ribozymes that specifically recognize and can cleave CKI nucleic acid molecules, particularly in the kinase region.

The invention also provides antibodies that selectively bind to CKI polypeptides, variants, and fragments and particularly to the kinase region.

The invention is also directed to pharmaceutical compositions containing the CKI variants, ribozymes capable of cleaving CKI MRNA, antisense polynucleotides capable of hybridizing to CKI nucleic acid, CKI antibodies, CKI non-antibody binding partners such as Dvl-1, GSK3, β-catenin, and Axin, and other CKI modulators.

The invention also provides vectors and host cells for expression of the CKI nucleic acid molecules, variants, and fragments and CKI polypeptides, variants, and fragments, and particularly recombinant vectors and host cells. The invention also provides pharmaceutical compositions containing the vectors and host cells that are useful in vivo to target cells in which Wnt signaling is to be disrupted.

The invention also provides methods for making the vectors and host cells and methods for using them to produce the CKI nucleic acid molecules and polypeptides and variants and fragments.

The invention also provides methods of screening for compounds that modulate the activity of the Wnt signal pathway by means of interaction with CKI. Accordingly, these compounds can modulate the activity of the CKI polypeptide directly or can modulate the expression of CKI nucleic acid encoding the CKI polypeptide.

The invention also provides a process for modulating CKI polypeptide activity or nucleic acid expression, particularly using the screened compounds, preferably to treat disorders mediated by Wnt signal transduction.

The invention thus provides a method for interfering with the Wnt signal pathway in a cell, especially in which the pathway is up-regulated, the method comprising administering to the cell the CKI polypeptides or nucleic acids and allowing the polypeptides or nucleic acids to interfere with the pathway.

The invention also provides a method for interfering with the Wnt signal pathway in vivo in a subject, especially in which the Wnt signal pathway is up-regulated, the method comprising administering to the subject any of the CKI polypeptides or nucleic acids described herein in amounts sufficient to interfere with the pathway.

The invention also provides diagnostic assays for determining the level of CKI polypeptides or nucleic acids in a biological sample or for determining the presence of a mutation in the CKI polypeptides or nucleic acids.

The invention also provides a method for detecting a CKI-mediated hyperproliferative disorder involving isolating a sample from a patient, tissue, or cell expressing the disorder, providing a molecule capable of binding to and forming a complex with CKI, contacting the CKI sample with the molecule under conditions allowing a complex to be formed, determining the amount of complex formed, and comparing the amount of complex formed with the amount of complex formed from a normal patient, tissue, or cell.

The invention is also directed to such methods in which the disorder is a Wnt-1 signal transduction mediated disorder.

In preferred embodiments, the molecule capable of binding to CKI is an anti-CKI antibody. In alternative embodiments of the invention, the binding molecule includes, but is not limited to, GSK3, Axin, β-catenin, and Dvl-1.

The invention is also directed to a method for detecting a CKI-mediated hyperproliferative disorder by obtaining a sample from a patient, tissue, or cell, expressing the disorder, contacting the sample with a CKI substrate capable of being phosphorylated by CKI, contacting the components under conditions that allow CKI phosphorylation of the substrate, and measuring the amount of phosphorylated substrate compared to a sample from a patient, tissue, or cell, not expressing the disorder.

In preferred embodiments of the invention, the substrate includes, but is not limited to, GSK3, Axin, β-catenin, and Dvl-1 gene product.

The invention is also directed to a method for detecting a Wnt-1 signal transduction-mediated disorder using the above method.

The invention is also directed to a method for detecting a CKI-mediated hyperproliferative disorder by identifying specific CKI variants that lead to hyperproliferation by providing a sample from a patient, tissue, or cell expressing the disorder and detecting the variation in the variant. Detection can be by means of specific antibodies developed against the variant, peptide analysis such as by proteolytic digestion and separation, altered binding properties to CKI binding partners, and nucleic acid analysis. Nucleic acid analysis involves DNA and RNA sequencing and genomic copy analysis.

The invention is also directed to a method for detecting a Wnt-1 signal transduction-mediated disorder using the above method.

The invention is also directed to a method for detecting a CKI-mediated hyperproliferative disorder by providing a polynucleotide capable of binding to CKI nucleic acid under stringent conditions, providing a sample from a patient, tissue, or cell expressing the disorder, contacting the sample with the polynucleotide under conditions permitting a hybrid to be formed between the polynucleotide and the CKI nucleic acid, determining the amount of hybrid formed and comparing this amount with the amount of hybrid formed from a normal tissue sample.

The invention is also directed to a method for detecting a Wnt-1 signal transduction-mediated disorder by the above method.

In preferred embodiments of the method, the polynucleotide is bound to CKI mRNA.

The invention is also directed to a method of detecting a CKI-mediated hyperproliferative disorder by providing a sample from a patient, tissue, or cell expressing the disorder, contacting the sample with a protein capable of phosphorylating CKI as a substrate, contacting the sample and protein under conditions permitting the protein to phosphorylate CKI and measuring the amount of phosphorylated CKI compared to the amount of phosphorylated CKI in a normal sample.

The invention is also directed to a method for detecting a Wnt-1 signal transduction mediated disorder using the above method.

The above method allows the detection of a CKI variant that is aberrantly phosphorylated and, as a result, leads to the disorder.

The invention is also directed to a method for treating a CKI-mediated hyperproliferative disorder by administering, to an animal with the disorder, an amount of CKI inhibitor effective to treat hyperproliferation.

The invention is also directed to a method for treating a Wnt-1 signal transduction mediated disorder in an animal by administering to the animal an amount of CKI inhibitor effective to treat the disorder.

The CKI inhibitor can include a kinase inhibitor, ribozyme capable of cleaving CKI mRNA, an anti-CKI antibody, and an antisense polynucleotide capable of hybridizing to CKI mRNA to effectively inhibit translation.

The invention is also directed to a method for treating a CKI-mediated hyperproliferative disorder by administering a CKI variant in an amount effective to decrease hyperproliferation.

The invention is also directed to a method for treating a Wnt-1 signal transduction mediated disorder by administering a CKI variant in an amount effective to treat the disorder.

Preferred variants include those that exhibit less kinase activity than CKI from patients, tissues, or cells not exhibiting the disorder, or which cannot be phosphorylated to the same level as that found in CKI from patients, tissues or cells not expressing the disorder.

The invention is directed to inhibiting hyperplasia, in one embodiment by inhibiting the Wnt pathway by means of CKI. In preferred embodiments, the hyperplasia results in a tumor. In highly preferred embodiments, the tumor is a malignant tumor. In highly preferred embodiments, the tumor is a breast or colon cancer or melanoma.

The invention encompasses the treatment and diagnosis of mammals and particularly of humans.

The invention encompasses all CKI isoforms and variants from any biological source including mammals, and particularly humans. Preferred is CKIε, especially as shown in SEQ ID NO:2.

Further, chimeric CKI variants can be provided in which the kinase or other functional region can be fused to heterologous CKI sequences, such as regions derived from other CKI isoforms from the same animal or other animals.

BRIEF DESCRIPTION OF THE DRAWINGS

FIGS. 2A–B. A) Luciferase activity transduced by CKIε was inhibited by cotransfected GSK3, while CKI lys→arg 38 did not inhibit the signal transduced by kinase-inactive GSK3 (DNGSK3). B) Luciferase activity transduced by Dvl-1 was inhibited by CKI lys→arg 38. C) CKIε phosphorylated GSK3 in an in vitro kinase assay. A truncated mutant, CKIεΔ, where the C-terminus was deleted had intact kinase activity. It was immunoprecipitated using anti-HA antibody and mixed with Immunoprecipitated GSK3.

FIGS. 3A–C Nucleotide sequence (sense sequence, SEQ ID NO:2; antisense sequence, SEQ ID NO:3) and deduced amino acid sequence (SEQ ID NO:1) of mouse CKIε.

DETAILED DESCRIPTION OF THE INVENTION

Figure 1A:
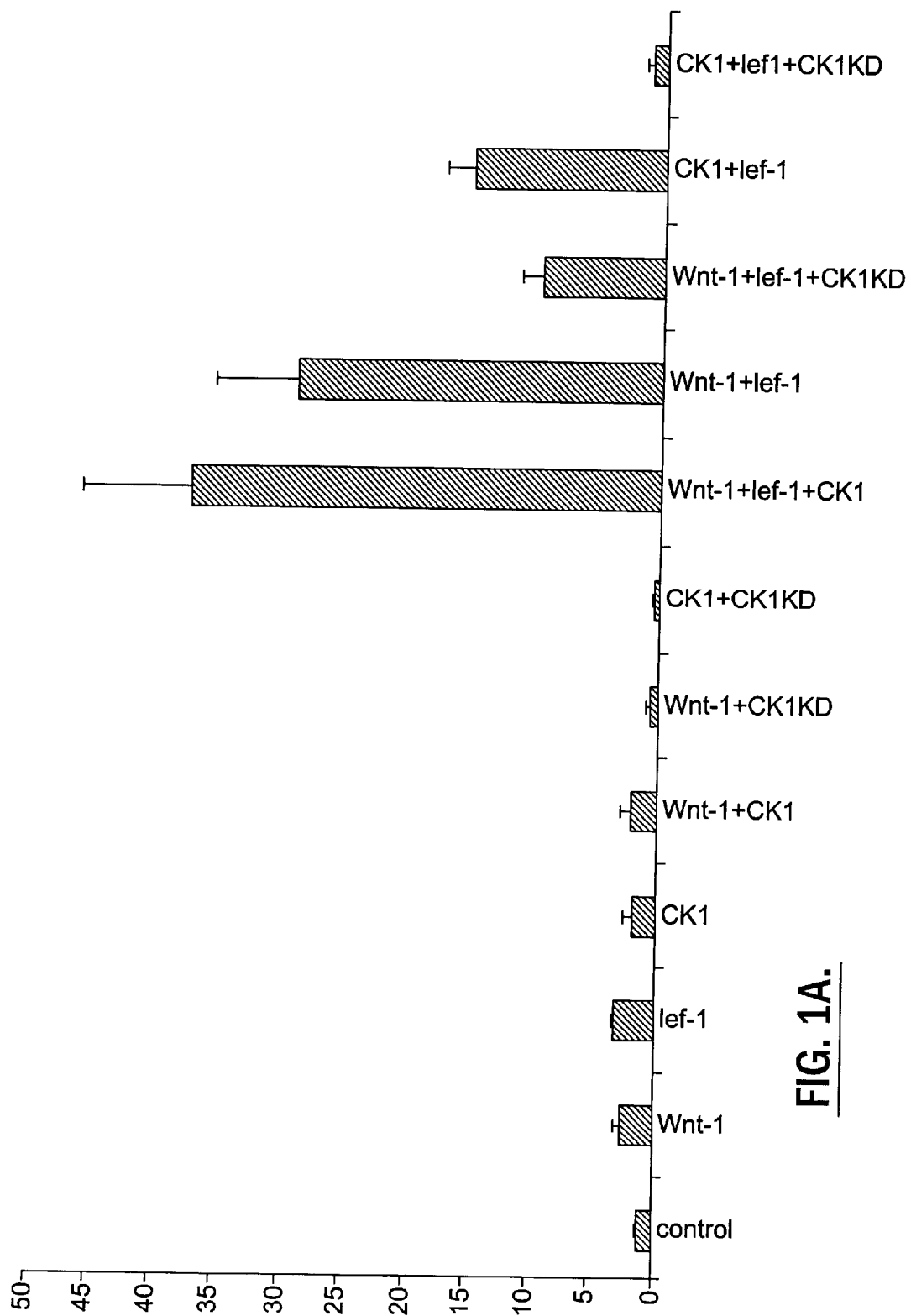
FIGS. 1A–B. A) A kinase-inactive mutant (CKIKD) of CKIε inhibits Wnt signaling in a Lef-luciferase assay. Combinations of Wnt-1, CKIε, CKI kinase dead variant (lys→arg 38) and Lef-1 were transfected into Cos cells with a luciferase gene driven by multiple copies of Lef enhancer elements. As an internal control of transfection efficiency, the β-galactosidase gene driven by the SV40 promoter was co-transfected in all samples. 24 hours after transfection, cells were lysed and the lysate was tested for luciferase activity. The luciferase activity was normalized with respect to β-galactosidase activity. B) CKIε RNA was able to rescue the dorsal structure of ventralized Xenopus embryo, while CKI lys→arg 38 failed to do so. Dorsoanterior index (DAI) grade numbers were assigned to the phenotypes of the embryos. A grade 5 embryo is normal; a grade 3 embryo is cyclopic (one eye); a grade 1 embryo has a tail fin and somites but no head (acephalic); and a grade 0 embryo has no dorsoanterior structures (Kao et al., 1988).
Figure 1B:
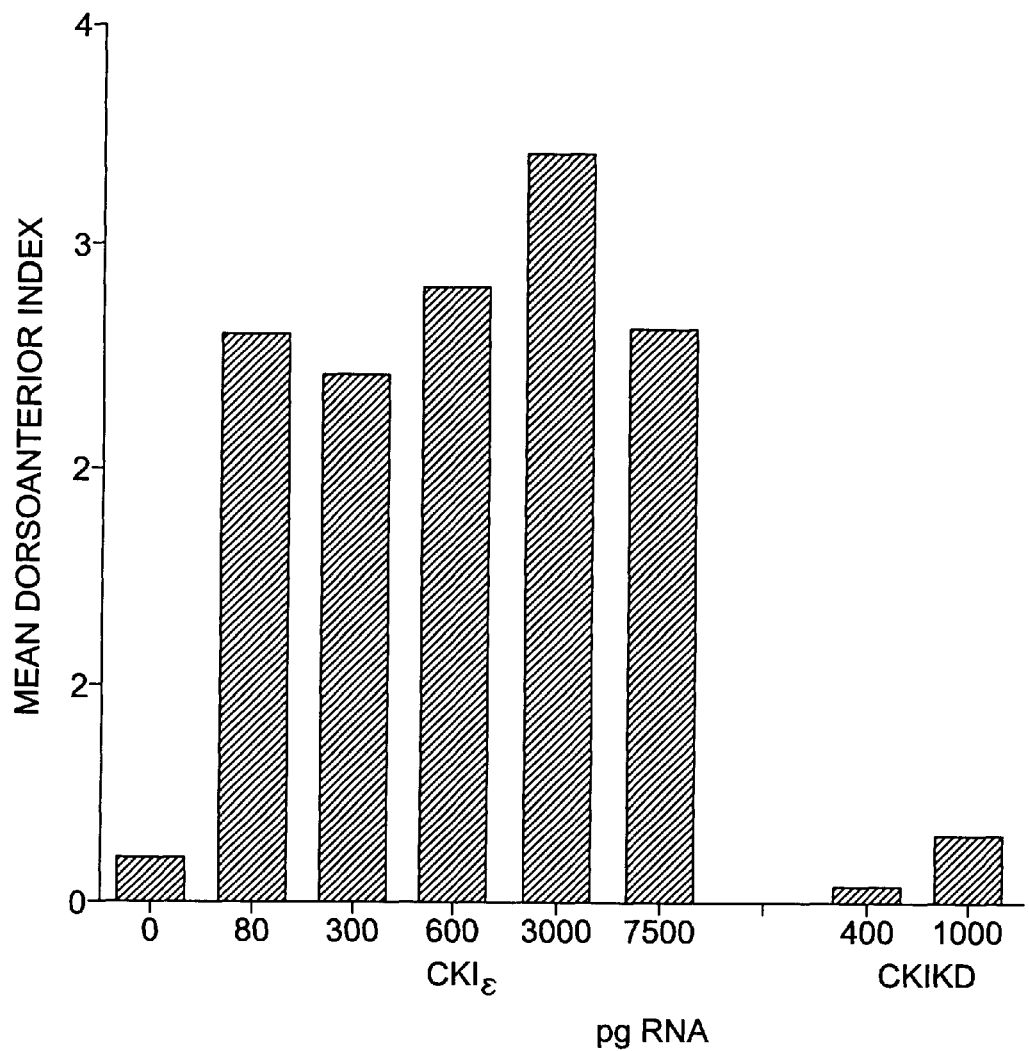

The present invention now will be described more fully. This invention may, however, be embodied in many different forms and should not be construed as limited to the embodiments set forth herein; rather, these embodiments are provided so that this disclosure will convey the invention to those skilled in the art.

COMPOSITIONS

Polypeptides

The present invention encompasses all CKI homologs, orthologs, and isoforms. It is specifically directed to the CKI of SEQ ID NO:1. The invention also provides isolated or purified CKI variant polypeptides.

As used herein a polypeptide is said to be "isolated" or "purified" when it is substantially free of cellular material, when it is isolated from recombinant and non-recombinant cells, or free of chemical precursors or other chemicals when it is chemically synthesized. A polypeptide, however, can be joined to another polypeptide with which it is not normally associated in a cell and still be considered isolated or purified.

Biologically active variants of a polypeptide of interest that serves as a therapeutically active component in the pharmaceutical compositions of the invention are also encompassed by the term "polypeptide" as used herein. Such variants should retain the desired biological activity of the native polypeptide such that the pharmaceutical composition comprising the variant polypeptide has the same therapeutic effect as the pharmaceutical composition comprising the native polypeptide when administered to a subject. Methods are available in the art for determining whether a variant polypeptide retains the desired biological activity, and hence serves as a therapeutically active component in the pharmaceutical composition. Biological activity can be measured using assays specifically designed for measuring activity of the native polypeptide or protein, including assays described in the present invention. Additionally, antibodies raised against a biologically active native polypeptide can be tested for their ability to bind to the variant polypeptide, where effective binding is indicative of a polypeptide having a conformation similar to that of the native polypeptide.

Suitable biologically active variants of a native or naturally occurring polypeptide of interest can be fragments, analogues, and derivatives of that polypeptide. By "fragment" is intended a polypeptide consisting of only a part of the intact polypeptide sequence and structure, and can be a C-terminal deletion or N-terminal deletion of the native polypeptide. By "analogue" is intended an analogue of either the native polypeptide or of a fragment of the native polypeptide, where the analogue comprises a native polypeptide sequence and structure having one or more amino acid substitutions, insertions, deletions, fusions, or truncations. "Muteins", such as those described herein, and peptides having one or more peptoids (peptide mimics) are also encompassed by the term analogue. By "derivative" is intended any suitable modification of the native polypeptide of interest, of a fragment of the native polypeptide, or of their respective analogues, such as glycosylation, phosphorylation, or other addition of foreign moieties, so long as the desired biological activity of the native polypeptide is retained. Methods for making polypeptide fragments, analogues, and derivatives are generally available in the art.

For example, amino acid sequence variants of the polypeptide can be prepared by mutations in the cloned DNA sequence encoding the native polypeptide of interest. Methods for mutagenesis and nucleotide sequence alterations are well known in the art. See, for example, Walker and Gaastra, eds. (1983) *Techniques in Molecular Biology* (MacMillan Publishing Company, New York); Kunkel (1985) *Proc. Natl. Acad. Sci. USA* 82:488–492; Kunkel et al. (1987) *Methods Enzymol.* 154:367–382; Sambrook et al. (1989) *Molecular Cloning: A Laboratory Manual* (Cold Spring Harbor, N.Y.); U.S. Pat. No. 4,873,192; and the references cited therein; herein incorporated by reference. Guidance as to appropriate amino acid substitutions that do not affect biological activity of the polypeptide of interest may be found in the model of Dayhoff et al. (1978) in *Atlas of Protein Sequence and Structure* (Natl. Biomed. Res. Found., Washington, D.C.), herein incorporated by reference. Conservative substitutions, such as exchanging one amino acid with another having similar properties, may be preferred. Examples of conservative substitutions include, but are not limited to, Gly⇌Ala, Val⇌Ile⇌Leu, Asp⇌Glu, Lys⇌Arg, Asn⇌Gln, and Phe⇌Trp⇌Tyr.

In constructing variants of the polypeptide of interest, modifications are made such that variants continue to possess the desired activity. Obviously, any mutations made in the DNA encoding the variant polypeptide must not place the sequence out of reading frame and preferably will not create complementary regions that could produce secondary mRNA structure. See EP Patent Application Publication No. 75,444.

Biologically active variants of a polypeptide of interest will generally have at least 70%, preferably at least 80%, more preferably about 90% to 95% or more, and most preferably about 98% or more amino acid sequence identity to the amino acid sequence of the reference polypeptide molecule, which serves as the basis for comparison. A biologically active variant of a native polypeptide of interest may differ from the native polypeptide by as few as 1–15 amino acids, as few as 1–10, such as 6–10, as few as 5, as few as 4, 3, 2, or even 1 amino acid residue. By "sequence identity" is intended the same amino acid residues are found within the variant polypeptide and the polypeptide molecule that serves as a reference when a specified, contiguous segment of the amino acid sequence of the variant is aligned and compared to the amino acid sequence of the reference molecule. The percentage sequence identity between two amino acid sequences is calculated by determining the number of positions at which the identical amino acid residue occurs in both sequences to yield the number of matched positions, dividing the number of matched positions by the total number of positions in the segment undergoing comparison to the reference molecule, and multiplying the result by 100 to yield the percentage of sequence identity.

For purposes of optimal alignment of the two sequences, the contiguous segment of the amino acid sequence of the variant may have additional amino acid residues or deleted amino acid residues with respect to the amino acid sequence of the reference molecule. The contiguous segment used for comparison to the reference amino acid sequence will comprise at least twenty (20) contiguous amino acid residues, and may be 30, 40, 50, 100, or more residues. Corrections for increased sequence identity associated with inclusion of gaps in the variant's amino acid sequence can be made by assigning gap penalties. Methods of sequence alignment are well known in the art for both amino acid sequences and for the nucleotide sequences encoding amino acid sequences.

Thus, the determination of percent identity between any two sequences can be accomplished using a mathematical algorithm. One preferred, non-limiting example of a mathematical algorithm utilized for the comparison of sequences is the algorithm of Myers and Miller (1988) *CABIOS* 4:11–17. Such an algorithm is utilized in the ALIGN program (version 2.0), which is part of the GCG sequence alignment software package. A PAM120 weight residue table, a gap length penalty of 12, and a gap penalty of 4 can be used with the ALIGN program when comparing amino acid sequences. Another preferred, nonlimiting example of a mathematical algorithm for use in comparing two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to a nucleotide sequence encoding the polypeptide of interest. BLAST protein searches can be performed with the XBLAST program, score=50, wordlength=3, to obtain amino acid sequences homologous to the polypeptide of interest. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., XBLAST and NBLAST) can be used. See www.ncbi.nlm.nih.gov. Also see the ALIGN program (Dayhoff(1978) in *Atlas of Protein Sequence and Structure* 5: Suppl. 3 (National Biomedical Research Foundation, Washington, D.C.) and programs in the Wisconsin Sequence Analysis Package, Version 8 (available from Genetics Computer Group, Madison, Wisconsin), for example, the GAP program, where default parameters of the programs are utilized.

When considering percentage of amino acid sequence identity, some amino acid residue positions may differ as a result of conservative amino acid substitutions, which do not affect properties of protein function. In these instances, percent sequence identity may be adjusted upwards to account for the similarity in conservatively substituted amino acids. Such adjustments are well known in the art. See, for example, Myers and Miller (1988) *Computer Applic. Biol. Sci.* 4:11–17.

The precise chemical structure of a polypeptide depends on a number of factors. As ionizable amino and carboxyl groups are present in the molecule, a particular polypeptide may be obtained as an acidic or basic salt, or in neutral form. All such preparations that retain their biological activity when placed in suitable environmental conditions are included in the definition of polypeptides as used herein. Further, the primary amino acid sequence of the polypeptide may be augmented by derivatization using sugar moieties (glycosylation) or by other supplementary molecules such as lipids, phosphate, acetyl groups and the like. It may also be augmented by conjugation with saccharides. Certain aspects of such augmentation are accomplished through post-translational processing systems of the producing host; other such modifications may be introduced in vitro. In any event, such modifications are included in the definition of polypeptide used herein so long as the activity of the polypeptide is not destroyed. It is expected that such modifications may quantitatively or qualitatively affect the activity, either by enhancing or diminishing the activity of the polypeptide, in the various assays. Further, individual amino acid residues in the chain may be modified by oxidation, reduction, or other derivatization, and the polypeptide may be cleaved to obtain fragments that retain activity. Such alterations that do not destroy activity do not remove the polypeptide sequence from the definition of polypeptide of interest as used herein.

The art provides substantial guidance regarding the preparation and use of polypeptide variants. In preparing the polypeptide variants, one of skill in the art can readily determine which modifications to the native protein nucleotide or amino acid sequence will result in a variant that is suitable for use as a therapeutically active component of a pharmaceutical composition of the present invention and whose aggregate formation is decreased by the presence of an amino acid base and an acid substantially free of its salt form, the salt form of the acid, or a mixture of the acid and its salt form, as described herein.

The CKI variant polypeptides are preferably purified to homogeneity. It is understood, however, that preparations in which the polypeptide is not purified to homogeneity are useful and considered to contain an isolated form of the polypeptide. The critical features that the preparation allows for the desired function of the polypeptide, even in the presence of considerable amounts of other components. Thus, the invention encompasses various degrees of purity. Degrees of purity can be preparations having less than about 30% dry weight other proteins, more preferably less than 20%, still more preferably less than 10%, and most preferably less than about 5%.

Variants can be naturally occurring or can be made by recombinant means or chemical synthesis to provide the useful and novel characteristics for the CKI polypeptide. Preferred variations include, but are not limited to, mutations in the kinase region that result in over- phosphorylation or under-phosphorylation of a CKI substrate or over- or under-phosphorylation of the CKI protein, itself. Highly preferred variants include kinase-dead mutants with changes in the region homologous to between amino acids 1–69 in SEQ ID NO:1, specifically at lysine 38, the kinase active site; mutants with a deletion of the C-terminal region homologous to amino acid 304 to the end in SEQ ID NO:1, comprising a potential phosphorylation site and important for CKI kinase specificity; a CKI polypeptide with additional terminal amino acid sequences added for the purpose of purification, such as a C-terminal extension of SYPYD-VPDYASLGGPS (SEQ ID NO:4), and HA epitope for immunoaffinity purification.

Polypeptide variants, as discussed, can be naturally occurring or can be constructed by recombinant or synthetic means. Naturally occurring variants include polypeptides encoded by orthologs, homologs, and allelic variants. Naturally occurring polypeptide variants contain at least about 85, 90, 95 and up to 99% homology to the amino acid sequence shown in SEQ ID NO:1. In preferred embodiments, however, the invention encompasses CKI natural variants having a kinase domain that is at least about 50, 60, 70, 80, 85, 90, 95, 98 and up to 100% homologous to the amino acid sequence shown in SEQ ID NO:1.

The invention also includes CKI wild-type polypeptide and variant fragments. Preferred fragments are derived from the kinase region.

Useful fragments also have immunogenic properties. These contain an epitope-bearing portion of the CKI polypeptide useful for raising antibodies that bind specifically to the CKI polypeptide, variant, region, or fragment. Preferred regions are derived from the kinase region.

By "fragment" is intended a peptide that is only a part of the intact CKI sequence and structure. It includes, but is not limited to, a C-terminal deletion or N-terminal deletion.

The term "fragment" is meant to include any portion of the protein which provides a segment that substantially or completely retains the biological function(s) of the protein (e.g., immunogenicity, catalytic activity, or ability to form a nucleic acid duplex). The term is meant to include fragments made from any source, such as, for example, from naturally-occurring peptide sequences, synthetic or chemically-synthesized peptide sequences, and genetically-engineered peptide sequences.

Peptides having one or more peptoids (peptide mimics) are also encompassed by the term (see International Publication No. WO 91/04282).

Fragments can be discrete (not fused to other amino acids or polypeptides) or can be within a larger polypeptide. Further, several fragments can be comprised within a single larger polypeptide. In one embodiment, a fragment designed for expression in a host can have heterologous pre- and pro-polypeptide regions fused to the amino terminus of the fragment and an additional region fused to the carboxyl terminus of the fragment.

The invention thus provides chimeric or fusion proteins. These comprise a CKI protein operatively linked to a heterologous protein. This indicates that the CKI protein and the heterologous protein are fused in frame. The heterologous protein can be fused to the N-terminus or C-terminus of the CKI protein.

In one embodiment, the fusion protein does not affect CKI function per se. For example, it can be a GST fusion protein useful for purification. Other types of fusion proteins include, but are not limited to, enzymatic fusion proteins, for example β-galactosidase fusions, yeast to hybrid GAL fusions, poly-His fusions and Ig fusions. Such fusions can facilitate the purification of recombinant CKI protein. In another embodiment, the fusion protein contains a heterologous signal sequence at its N-terminus.

The chimeric or fusion proteins can be produced by standard recombinant DNA techniques. For example, DNA fragments are ligated together in frame in accordance with conventional techniques. In another embodiment, the fusion protein can be synthesized by conventional techniques using automated DNA synthesizers. Alternatively, PCR amplification of gene fragments can be carried out using anchor primers giving rise to complementary overhangs between two consecutive gene fragments that can subsequently be reannealed and reamplified to generate a chimeric gene sequence. Moreover, many expression vectors are commercially available that already encode a fusion moiety.

Another form of fusion protein directly affects receptor functions. Accordingly, a CKI polypeptide encompassed by the present invention can be used to make a chimeric protein in which the C-terminal region and kinase domain are heterologous to one another.

Isolated CKI variants can be purified from cells that naturally express it or from recombinant cells that have been modified to contain and express the CKI polypeptide, variant, or fragment. Preferably, the polypeptide is produced by recombinant DNA techniques.

For example, a nucleic acid molecule encoding the CKI polypeptide is cloned into an expression vector, the expression vector introduced into a host cell, and the protein expressed in the host cell. The protein can then be isolated from the cell by an appropriate purification scheme using standard protein purification techniques.

The invention also encompasses polypeptide derivatives. By "derivative" is intended any suitable modification of CKI, CKI fragments, or their respective variants, such as glycosylation, phosphorylation, pegylation, or other addition of foreign moieties, so long as the relevant function is substantially or completely retained.

As used herein, the term is also meant to include a chemical derivative of a compound. Such derivatives may improve the compound's solubility, absorption, biological half life, etc. The derivatives may also decrease the toxicity of the molecule, or eliminate or attenuate any undesirable side effect of the molecule, etc. Derivatives and specifically, chemical moieties capable of mediating such effects are disclosed in *Remington's Pharmaceutical Sciences* (1980). Procedures for coupling such moieties to a molecule are well known in the art.

Methods for making CKI fragments, variants, and derivatives are available in the art. See generally U.S. Pat. Nos. 4,738,921, 5,158,875, and 5,077,276; International Publication Nos. WO 85/00831, WO 92/04363, WO 87/01038, and WO 89/05822; and European Patent Nos. EP 135094, EP 123228, and EP 128733; herein incorporated by reference.

The polypeptides are useful for producing antibodies specific for the polypeptides, regions of the polypeptides, or against fragments.

The polypeptides are also useful in drug screening assays in cell-based or cell-free systems. They can be used to identify compounds that interact with the CKI polypeptide and/or affect Wnt signal transduction. Thus, the CKI protein and appropriate variants and fragments can be used in high throughput screens to assay candidate compounds for the ability to bind. They can then be further screened against a system that allows signal transduction to determine the effect of the compound on the pathway. Compounds can be identified that activate or suppress the pathway. The endpoint for identification of compounds that modulate CKI and signal transduction can also involve an assay of events in the signal transduction pathway. This includes, for example, transcription from the Lef-1 promoter, which in one embodiment can be linked to a marker that is easily detectable, such as luciferase. Alternatively, phosphorylation of CKI or a CKI protein target can also be measured.

The CKI polypeptides are also useful in competition binding assays designed to discover compounds that interact with the CKI protein. Thus, a compound is exposed to a CKI polypeptide under conditions that allow the compound to bind or otherwise interact with the polypeptide. Soluble CKI polypeptide is also added to the mixture. If the test compound interacts with the soluble CKI polypeptide, it decreases the amount of complex formed or activity from the target.

These modulators of CKI protein activity identified in the drug screening assays can be used to treat a subject with a disorder mediated by CKI. These methods of treatment include the steps of administering the modulators in a pharmaceutical composition to a subject in need of treatment.

The CKI polypeptides are also useful to provide a target for diagnosis of a disorder involving CKI.

Antibodies

The invention also provides antibodies that selectively bind to the CKI protein and its variants and fragments. An antibody is considered to selectively bind even if it also binds to other proteins not substantially homologous with the CKI protein. These other proteins could share homology with a fragment or domain of the CKI protein. This conservation in specific regions gives rise to antibodies that bind to both proteins by virtue of the homologous sequence. However, it would be understood that antibody binding to the receptor protein is still selective.

Antibodies can be polyclonal or more preferably monoclonal. An intact antibody, or fragment thereof, can be used.

Polynucleotides

The invention provides isolated CKI variant polynucleotides. An isolated nucleic acid is separated from other nucleic acids present in the natural source of the CKI nucleic acid. Preferably, an isolated nucleic acid is free of sequences that naturally flank it (located at the 5' and 3' ends) in the genomic DNA of the organism from which the nucleic acid is derived. However, there can be some flanking nucleotide sequences, for example, up to about 5KB. The important point is that the nucleic acid is isolated from flanking sequences such that it can be subjected to specific manipulations described herein, such as recombinant expression, preparation of probes and primers, and other uses specific to the CKI nucleic acid sequences.

For example, recombinant CKI DNA molecules contained in a vector are considered isolated. Further examples of isolated CKI nucleic acid include recombinant DNA molecules maintained in heterologous host cells or purified DNA molecules in solution. Isolated RNA molecules include in vivo or in vitro RNA transcripts of the isolated DNA molecules of the present invention. Further, isolated nucleic acid molecules include those produced synthetically.

Fragments and variants of the disclosed nucleotide sequences are also encompassed by the present invention. By "fragment" is intended a portion of the nucleotide sequence. Fragments of a nucleotide sequence may encode protein fragments that retain the biological activity of the native protein. Alternatively, fragments of a nucleotide sequence that are useful as hybridization probes generally do not encode proteins that retain biological activity. Thus, fragments of a nucleotide sequence may range from at least about 20 nucleotides, about 50 nucleotides, about 100 nucleotides, and up to the full-length nucleotide sequence of the invention.

A fragment of a CKI nucleotide sequence that encodes a biologically active portion of a protein of the invention will encode at least 15, 25, 30, 50, 100, 150, 200, or 250 contiguous amino acids, or up to the total number of amino acids present in a full-length CKI protein of the invention.

Thus, a fragment of a nucleotide sequence may encode a biologically active portion of a CKI protein, or it may be a fragment that can be used as a hybridization probe or PCR primer using methods disclosed below. A biologically active portion of a CKI protein can be prepared by isolating a portion of one of the CKI nucleotide sequences of the invention, expressing the encoded portion of the CKI protein (e.g., by recombinant expression in vitro), and assessing the activity of the encoded portion of the protein. Nucleic acid molecules that are fragments of a CKI nucleotide sequence comprise at least 16, 20, 50, 75, 100, 150, 200, 250, 300, 350, 400, 450, 500, 550, 600, 650, 700, 800, 900, 1,000, 1,100, 1,200 nucleotides, or up to the number of nucleotides present in a full-length nucleotide sequence disclosed herein.

By "variants" is intended substantially similar sequences. Variant nucleotide sequences also include synthetically derived nucleotide sequences, such as those generated, for example, by using site-directed mutagenesis but which still encode a CKI protein of the invention. Generally, variants of a particular nucleotide sequence of the invention will have at least 40%, 50%, 60%, 70%, generally at least 75%, 80%, 85%, preferably about 90% to 95% or more, and more preferably about 98% or more sequence identity to that particular nucleotide sequence as determined by sequence alignment programs described elsewhere herein using default parameters.

The nucleotide sequences of the invention can be used to isolate corresponding sequences. In this manner, methods such as PCR, hybridization, and the like can be used to identify such sequences based on their sequence homology to the sequence set forth herein. Sequences isolated based on their sequence identity to the entire CKI sequence set forth herein or to fragments thereof are encompassed by the present invention.

In a PCR approach, oligonucleotide primers can be designed for use in PCR reactions to amplify corresponding DNA sequences from cDNA or genomic DNA. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York).

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Duration of hybridization is generally less than about 24 hours, usually about 4 to about 12 hours.

The CKI polynucleotides can encode the CKI sequences and heterologous sequences that can play a role in processing of a protein from precursor to mature form, facilitate protein trafficking, prolong or shorten protein half-life, or facilitate manipulation of a protein for assay or production.

The variant polynucleotides can be in the form of RNA such as mRNA or in the form of DNA, including cDNA and genomic DNA obtained by cloning or produced by chemical synthetic techniques or by a combination thereof. The nucleic acid can be double stranded or single stranded. Single stranded nucleic acid can include the coding strand or the non-coding strand. A preferred nucleic acid encodes the preferred polypeptide variants described herein.

The polynucleotides can be naturally occurring, such as allelic variants, can be derived from a different locus in the same organism, or from another organism. Alternatively, they can be constructed by recombinant DNA methods or by chemical synthesis. The variants can contain nucleotide substitutions, deletions, inversions, and insertions. Preferred variations occur in the kinase regions that provide the ability of CKI to phosphorylate a substrate or alternatively provide the capability of being phosphorylated itself.

The invention provides polynucleotides comprising a fragment of the full length CKI or variant. The fragment can be single or double stranded and can comprise DNA or RNA. The fragments can also encode epitope bearing regions of the CKI polypeptides discussed herein. The polynucleotide sequences and fragments are useful, among other things, as probes and primers.

The CKI nucleic acid also provides a target for identifying a compound that can be used to treat a disorder associated with CKI. The method includes assaying the ability of the compound to modulate the expression of the CKI nucleic acid and thus identifying a compound that can be used to treat the disorder.

CKI nucleotide variants that are useful according to the invention, as discussed, can be naturally occurring or synthesized by recombinant or chemical methods. Naturally occurring variants (orthologs, homologs, and allelic variants) can be identified using standard cloning methods and any of the CKI isoform nucleic acids as a probe. These variants comprise a nucleic acid sequence encoding a CKI polypeptide that is at least about 85–98.9% homologous to the amino acid sequence shown in SEQ ID NO:1. The invention encompasses other preferred natural variants, specifically nucleic acid variants encoding CKI polypeptides in which the kinase domain is 50–100% homologous to the amino acid sequence shown in SEQ ID NO:1.

The nucleotide sequence for the CKI gene, as well as any variant thereof, is useful when operably linked to a promoter. In this manner, CKI nucleotide sequences are provided in expression cassettes for expression in vitro or in vivo to affect Wnt signaling.

Expression cassettes will comprise a transcriptional initiation region linked to the nucleotide sequence for the native CKI gene or variants thereof An expression cassette can be provided with a plurality of restriction sites for insertion of the nucleotide sequence to be under the transcriptional regulation of the regulatory regions. The expression cassette may additionally contain selectable marker genes.

The transcriptional initiation region, the inducible promoter, may be native or heterologous to the CKI. Additionally, the promoter may be the natural sequence or a synthetic sequence. As used herein, a chimeric gene comprises a coding sequence operably linked to transcription initiation region that is heterologous to the coding sequence. The transcriptional cassette will include, in the 5'-to-3' direction of transcription, a transcriptional and translational initiation region, a DNA sequence for the CKI gene, and a functional transcriptional and translational termination region. The termination region may be native with the transcriptional initiation region, may be native with the DNA sequence of interest, or may be derived from another source.

Additional sequence modifications are known to enhance gene expression in a host. These include elimination of sequences encoding spurious polyadenylation signals, exon-intron splice site signals, transposon-like repeats, and other such well-characterized sequences which may be deleterious to gene expression.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, for example, transitions and transversions, may be involved.

Genetic engineering by recombinant DNA techniques can be the most efficient way of producing CKI. Human DNA sequences encoding CKI are known and can be introduced into host cells for expression. CKI can be produced by recombinant DNA techniques in *E. coli*, yeast, insect, and mammalian cells. Secreted CKI can be made by adding a signal sequence to the DNA sequence encoding CKI. In addition, the DNA sequence encoding CKI can be manipulated to make CKI fragments, analogs, or derivatives. Such recombinant DNA techniques are generally available in the art. See, for example, International Publication No. WO 96/07424, where a recombinant human protein is produced in yeast.

"Expression vector" refers to a recombinant nucleic acid molecule (DNA or RNA) capable of directing expression of one or more heterologous genes encoding an antigen. The expression vector must include a promoter (unless the expression vector is designed for position-specific integration adjacent to a functional promoter) operably linked to the antigen-encoding gene(s), and a polyadenylation sequence. The expression vector can be part of a plasmid, virus, or other nucleic acid construct. In addition to the expression vector components, the vector construct may also include one or more of the following: a bacterial origin of replication; one or more selectable markers; a signal which allows the construct to exist as single-stranded DNA (e.g., an M13 origin of replication); a multiple cloning site; and a "mammalian" origin of replication (e.g., an SV40 or adenovirus origin of replication). In other embodiments, the expression vector is a recombinant viral genome, and will be either RNA or DNA, depending on the particular viral system being utilized. Alternatively, the expression vector may comprise in vitro transcribed RNA. As used herein, "expression vector" also refers to a vector which, after introduction into a cell, is converted to a different form. For example, the RNA genome carried a recombinant retrovirus is reverse transcribed into DNA and integrated into the genome of the cell. For purposes of this invention, both RNA and DNA forms are "expression vectors."

A "promoter" is an array of nucleic acid control sequences which direct transcription of a nucleic acid. As used herein, a promoter includes necessary nucleic acid sequences near the start site of transcription, such as, in the case of a polymerase II type promoter, a TATA element. The promoter also optionally includes distal enhancer or repressor elements which can be located as much as several thousand base pairs from the start site of transcription. A "constitutive" promoter is a promoter which is active under most environmental conditions and states of development or cell differentiation. An "inducible" promoter responds to an extracellular stimulus.

In vitro amplification techniques suitable for amplifying sequences to be subcloned into an expression vector are known. Examples of techniques sufficient to direct persons of skill through such in vitro amplification methods, including the polymerase chain reaction (PCR) the ligase chain reaction (LCR), Qβ-replicase amplification and other RNA polymerase mediated techniques (e.g., NASBA) are found in Sambrook et al. *Molecular Cloning—A Laboratory Manual* (2nd Ed) Vol. 1–3 (1989); U.S. Pat. No. 4,683,202; *PCR Protocols A Guide to Methods and Applications* (Innis et al. eds) Academic Press Inc. San Diego, Calif. (1990) (Innis); Arnheim & Levinson (Oct. 1, 1990) C&*EN*36–47; *The Journal Of NIH Research* (1991) 3, 81–94; Kwoh el al. *Proc. Natl. Acad Sci. USA* 86, 1173 (1989); Guatelli et al. *Proc. Natl. Acad Sci. USA* 87,1874 (1990); Lomell et al. *J. Clin. Chem*. 35:1826 (1989); Landegren et al., *Science* 241, 1077–1080 (1988); Van Brunt *Biotechnology* 8:291–294 (1990); Wu and Wallace, *Gene* 4:560 (1989); Barringer et al. *Gene* 89:117 (1990), and Sooknanan et al. *Biotechnology* 13:563–564 (1995). Improved methods of cloning in vitro amplified nucleic acids are described in U.S. Pat. No. 5,426,039.

The term "recombinant" when used with reference to a cell indicates that the cell replicates or expresses a nucleic acid, or expresses a peptide or protein encoded by a nucleic acid whose origin is exogenous to the cell. Recombinant cells can express genes that are not found within the native (non-recombinant) form of the cell. Recombinant cells can also express genes found in the native form of the cell wherein the genes are re-introduced into the cell by artificial means, for example under the control of a heterologous promoter or other regulatory sequence.

The term "heterologous" when used with reference to a nucleic acid indicates that the nucleic acid comprises two or more subsequences which are not found in the same relationship to each other in nature. For instance, the nucleic acid is typically recombinantly produced, having two or more sequences derived from unrelated genes arranged to make a new functional nucleic acid. For example, in one embodiment, the nucleic acid has a promoter from one gene arranged to direct the expression of a coding sequence from a different gene. When used with reference to a protein, the term "heterologous" means that the protein is expressed in a cell or location where it is not ordinarily expressed in nature, such as in a recombinant cell which encodes the protein in an expression cassette.

METHODS OF DIAGNOSIS

Polynucleotides

CKI polynucleotide variants associated with a disorder can be identified by various methods known in the art. These include direct physical sequencing, the ability of the nucleic acid to produce normal levels of a CKI polypeptide or to produce a normal CKI (non-mutant) polypeptide, the ability of the nucleic acid to be cleaved by a ribozyme specific for the normal CKI nucleic acid, nuclease cleavage experiments designed to identify mismatch, assay of CKI nucleic acid levels, including mRNA and DNA, chromosome or tissue distribution relative to normal, and subcellular localization relative to normal.

It is also understood that any of these methods can also be used to diagnose a disorder mediated by CKI and/or disorders in the Wnt pathway. Thus, a biological sample obtained from a subject with a disorder is subjected to one or more of the assays and the results compared with those obtained from a subject not having the disorder.

With respect to disorders in a Wnt pathway, lesions in CKI could also be indirectly detected by analyzing the target nucleic acid or protein levels or phosphorylation status. Preferred targets include GSK3 and β-catenin. Other targets include Dvl-1 and Lef-1-mediated transcription.

Polynucleotide Hybridization Assay

Polynucleotide probes comprising at least 12 contiguous nucleotides selected from the nucleotide sequence shown in SEQ ID NO:2 are used for a variety of purposes, including identification of human chromosomes and determining transcription levels. Preferred regions of the native or variant CKI sequences have been discussed above and are found further in the Examples.

The nucleotide probes are labeled, for example, with a radioactive, fluorescent, biotinylated, or chemiluminescent label, and detected by well known methods appropriate for the particular label selected. Protocols for hybridizing nucleotide probes to preparations of metaphase chromosomes are also well known in the art. A nucleotide probe will hybridize specifically to nucleotide sequences in the chromosome preparations which are complementary to the nucleotide sequence of the probe. A probe that hybridizes specifically to a native CKI polynucleotide should provide a detection signal at least 5-, 10-, or 20-fold higher than the background hybridization provided with other unrelated sequences.

Nucleotide probes are used to detect expression of a gene corresponding to the CKI. For example, in Northern blots, mRNA is separated electrophoretically and contacted with a probe. A probe is detected as hybridizing to an mRNA species of a particular size. The amount of hybridization is quantitated to determine relative amounts of expression, for example under a particular condition. Probes are also used to detect products of amplification by polymerase chain reaction. The products of the reaction are hybridized to the probe and hybrids are detected. Probes are used for in situ hybridization to cells to detect expression. Probes can also be used in vivo for diagnostic detection of hybridizing sequences. Probes are typically labeled with a radioactive isotope. Other types of detectable labels may be used such as chromophores, fluors, and enzymes.

Expression of specific mRNA can vary in different cell types and can be tissue specific. This variation of mRNA levels in different cell types can be exploited with nucleic acid probe assays to determine tissue types or diseased tissues. For example, PCR, branched DNA probe assays, or blotting techniques utilizing nucleic acid probes substantially identical or complementary to polynucleotides listed in SEQ ID NO:2 can determine the presence or absence of CKI cDNA or mRNA.

Examples of a nucleotide hybridization assay are described in Urdea et al., PCT WO92/02526 and Urdea et al., U.S. Pat. No. 5,124,246, both incorporated herein by reference. The references describe an example of a sandwich nucleotide hybridization assay.

Alternatively, the Polymerase Chain Reaction (PCR) is another means for detecting small amounts of target nucleic acids, as described in Mullis et al., *Meth. Enzymol.* (1987) 155:335–350; U.S. Pat. No. 4,683,195; and U.S. Pat. No. 4,683,202, all incorporated herein by reference. Two primer polynucleotides nucleotides hybridize with the target nucleic acids and are used to prime the reaction. The primers may be composed of sequence within or 3' and 5' to the polynucleotides of the Sequence Listing. Alternatively, if the primers are 3and 5to these polynucleotides, they need not hybridize to them or the complements. A thermostable polymerase creates copies of target nucleic acids from the primers using the original target nucleic acids as a template. After a large amount of target nucleic acids is generated by the polymerase, it is detected by methods such as Southern blots. When using the Southern blot method, the labeled probe will hybridize to a polynucleotide of the Sequence Listing or complement.

Furthermore, mRNA or cDNA can be detected by traditional blotting techniques described in Sambrook et al., "*Molecular Cloning: A Laboratory Manual*" (New York, Cold Spring Harbor Laboratory, 1989). mRNA or cDNA generated from mRNA using a polymerase enzyme can be purified and separated using gel electrophoresis. The nucleic acids on the gel are then blotted onto a solid support, such as nitrocellulose. The solid support is exposed to a labeled probe and then washed to remove any unhybridized probe. Next, the duplexes containing the labeled probe are detected. Typically, the probe is labeled with radioactivity.

Stringency Definitions

"Homology" refers to the degree of similarity between x and y. The correspondence between the sequence from one form to another can be determined by techniques known in the art. For example, they can be determined by a direct comparison of the sequence information of the polynucleotide. Typically, two sequences, either polynucleotide or polypeptide, are homologous if the sequences exhibit at least 45% sequence identity; more typically, 50% sequence identity; more typically, 55% sequence identity; more typically, 60% sequence identity; more typically, 65% sequence identity; even more typically, 70% sequence identity. Usually, two sequences are homologous if the sequences exhibit at least 75% sequence identity; more usually, 80% sequence identity; even more usually, 85% sequence identity; even more usually, 90% sequence identity; and even more usually, 95% sequence identity.

Alternatively, homology can be determined by hybridization of the polynucleotides under conditions which form stable duplexes between homologous regions. Stable duplexes are those, for example, which would withstand digestion with a single-stranded specific nuclease(s), such as $S_1$. Such duplexes can be analyzed by various methods, such as size determination of digested fragments.

"Hybridization" refers to the association of two nucleic acid sequences to one another by hydrogen bonding. Typically, one sequence will be fixed to a solid support and the other will be free in solution. Then, the two sequences will be placed in contact with one another under conditions that favor hydrogen bonding. Factors that affect this bonding include: the type and volume of solvent; reaction temperature; time of hybridization; agitation; agents to block the non-specific attachment of the liquid phase sequence to the solid support (Denhardt's reagent or BLOTTO); concentration of the sequences; use of compounds to increase the rate of association of sequences (dextran sulfate or polyethylene glycol); and the stringency of the washing conditions following hybridization. See Sambrook, et al., MOLECULAR CLONING; A LABORATORY MANUAL, SECOND EDITION (1989), Volume 2, chapter 9, pages 9.47 to 9.57.

"Stringency" refers to conditions in a hybridization reaction that favor association of very similar sequences over sequences that differ. For example, the combination of temperature and salt concentration should be chosen that is approximately 12° to 20° C. below the calculated $T_m$ of the hybrid under study. The temperature and salt conditions can often be determined empirically in preliminary experiments in which samples of genomic DNA immobilized on filters are hybridized to the sequence of interest and then washed under conditions of different stringencies. See Sambrook, et al., above at page 9.50.

Variables to consider when performing, for example, a Southern blot are (1) the complexity of the DNA being blotted and (2) the homology between the probe and the sequences being detected. The total amount of the fragment (s) to be studied can vary a magnitude of 10, from 0.1 to 1 µg for a plasmid or phage digest to 10–9 to 10–8 µg for a single copy gene in a highly complex eukaryotic genome. For lower complexity polynucleotides, substantially shorter blotting, hybridization, and exposure times, a smaller amount of starting polynucleotides, and lower specific activity of probes can be used. For example, a single-copy yeast gene can be detected with an exposure time of only 1 hour starting with 1 µg of yeast DNA, blotting for two hours, and hybridizing for 4–8 hours with a probe of $10^8$ cpm/µg. For a single-copy mammalian gene a conservative approach would start with 10 µg of DNA, blot overnight, and hybridize overnight in the presence of 10% dextran sulfate using a probe of greater than $10^8$ cpm/µg, resulting in an exposure time of ~24 hours.

Several factors can affect the melting temperature (Tm) of a DNA-DNA hybrid between the probe and the fragment of interest, and consequently, the appropriate conditions for hybridization and washing. In many cases the probe is not 100% homologous to the fragment. Other commonly encountered variables include the length and total G+C content of the hybridizing sequences and the ionic strength and formamide content of the hybridization buffer. The effects of all of these factors can be approximated by a single equation:

$$Tm=81+16.6(\log 10C_i)+0.4[\%G+C)]-0.6(\%\text{formamide})-600/n-1.5(\%\text{mismatch})$$

where $C_i$ is the salt concentration (monovalent ions) and n is the length of the hybrid in base pairs (slightly modified from Meinkoth and Wahl, (1984) Anal. Biochem. 138: 267–284).

In designing a hybridization experiment, some factors affecting nucleic acid hybridization can be conveniently altered. The temperature of the hybridization and washes and the salt concentration during the washes are the simplest to adjust. As the temperature of the hybridization increases (i.e., stringency), it becomes less likely for hybridization to occur between strands that are nonhomologous, and as a result, background decreases. If the radio labeled probe is not completely homologous with the immobilized fragment (as is frequently the case in gene family and interspecies hybridization experiments), the hybridization temperature must be reduced, and background will increase. The temperature of the washes affects the intensity of the hybridizing band and the degree of background in a similar manner. The stringency of the washes is also increased with decreasing salt concentrations.

In general, convenient hybridization temperatures in the presence of 50% formamide are 42° C. for a probe with is 95% to 100% homologous to the target fragment, 37° C. for 90% to 95% homology, and 32° C. for 85% to 90% homology. For lower homologies, formamide content should be lowered and temperature adjusted accordingly, using the equation above. If the homology and between the probe and the target fragment are not known, the simplest approach is to start with both hybridization and wash conditions which are non-stringent. If nonspecific bands or high background are observed after autoradiography, the filter can be washed at high stringency and reexposed. If the time required for exposure makes this approach impractical, several hybridization and/or washing stringencies should be tested in parallel.

Nucleic acid hybridization is also useful in a diagnostic context using in situ hybridization methods. Thus, nucleic acid probes and primers allow the determination of the chromosomal position of CKI polynucleotides.

In situ hybridization also provides a method for quantitating gene copy number in situ. Thus, the probes are useful to determine patterns of the presence of the gene encoding the CKI polypeptides and their variants with respect to tissue distribution, for example whether gene duplication has occurred and whether the duplication occurs in all or only a subset of tissues.

The probes can also be used in this manner to determine levels of receptor nucleic acid expression in a cell, particularly in a biopsy of a patient.

The nucleic acid whose level is determined can be DNA or RNA.

Accordingly, the probes can be used to assess gene copy number in a given cell, tissue, or organism. This is particularly relevant where there has been an amplification of the CKI genes. A probe can be also used to assess the position of extra copies of the CKI genes as on extrachromosomal elements or as integrated into chromosomes in which the CKI gene is not normally found, for example as a homogenously staining region.

The polynucleotides are also useful to monitor the effectiveness of modulating compounds on the expression or activity of the CKI gene in clinical trials or in a treatment regimen. Thus, the gene expression pattern can serve as a barometer for the continuing effectiveness of treatment and particularly with compounds to which a patient can develop resistance.

The polynucleotides can also be used as hybridization probes to detect naturally occurring genetic mutations in the CKI gene and thereby determining whether a subject with a mutation is at risk for a disorder mediated by the Wnt pathway. Thus, a subject known to have, or predisposed to have, a Wnt signal pathway disorder can be diagnosed using the CKI polynucleotides and variant polynucleotides described herein.

Polypeptides

Variant CKI polypeptides that result in a disorder can be detected by various methods well known in the art. These include direct sequence analysis, the ability to phosphorylate a substrate or target, the ability to be phosphorylated, especially by a target, the ability to bind targets, the ability to bind antibodies specific for a normal CKI, the phosphorylation state of the CKI, the phosphorylation state of CKI targets, the amount of CKI targets, the ability to promote axis formation in Xenopus, and various physical parameters, such as pattern on gel electrophoresis. Preferred targets include GSK3 and β-catenin. Other targets, however, include Axin, β-catenin, Dvl-1 and transcription from the Lef-1 promoter.

It is understood that all of these methods are also applicable to diagnose CKI-mediated disorders and/or disorders in the Wnt pathway.

The CKI polypeptides are thus useful to provide a target for diagnosing disease, especially mediated by the Wnt receptor pathway. Useful methods detect the presence or levels of the CKI protein in a cell, tissue, or organism. A biological sample is contacted with a compound capable of interacting with the CKI protein such that the interaction can be detected.

Although a preferred agent for detecting the CKI protein is an antibody (see below), any molecule interacting with CKI, such as those compounds discovered through drug screening assays, is useful for detecting the protein.

The protein can be used to diagnose active disease or predisposition to disease in a patient having a variant CKI protein. Thus, the protein can be isolated, and assayed for the presence of a genetic mutation in a patient having a disorder, especially a disorder characterized by aberrant Wnt signal pathway transduction. Analytic methods include alter electrophoretic mobility, altered tryptic peptide digest, altered activity such as the ability to phosphorylate or be phosphorylated, alteration in antibody binding pattern, altered isoelectric point, direct amino acid sequencing, and any of the known assay techniques useful for detecting mutations in a protein.

The polypeptides are also a useful target for monitoring therapeutic effects during treatment for a disorder, especially Wnt signal pathway associated disorder. Thus, the therapeutic effectiveness of an agent designed to increase or decrease gene expression, protein levels, or CKI activity can be monitored over the course of treatment using the CKI polypeptides as an endpoint target.

Kinase Assays

CKI is a substrate for phosphorylation by other proteins and itself is capable of phosphorylating other protein substrates. Accordingly, kinase assays are based on phosphorylation by other proteins and phosphorylation by CKI of other substrates. Diagnostic assays of CKI mediated disorders are generally directed to the detection of CKI that is over expressed or CKI variants in which a mutation in kinase activity (either the ability to phosphorylate or the ability to be phosphorylated) leads to the disorder. Therefore, in a sample to be tested, a molecule such as a protein phosphorylating CKI or a substrate phosphorylated by CKI can be added. Then, the amount of phosphorylated CKI or of phosphorylated CKI substrate can be compared to a control sample derived from tissue or cells not exhibiting the disorder. It is understood, however, that it may not be the total amount that is dispositive but the rate of phosphorylation could also be effected. Accordingly, such assays may not be allowed to proceed to saturation.

CKI is stimulated by insulin, IL-I, and tumor necrosis factor (Cobb et al., *J. Biol. Chem.* 258:12472–12481 (1983); Guesdon et al., *J. Biol. Chem.* 268:4236–4243 (1993); Guy et al., *J. Biol. Chem.* 266:14343–14352 (1991)). In addition, the DNA-binding activity of the transcription factor CREM (cAMP responsive element modulator) is inhibited through its phosphorylation by CKI (DeGroot et al., *EMBO J.* 12:3903–3911 (1993)). Phosphorylation of glycogen synthase by CKI inhibits activity (Ahmad et al., *J. Biol. Chem.* 259:3420–3428 (1984); Flotow et al., *J. Biol. Chem.* 264:9126–9128 (1989); Roach, *J. Biol. Chem.* 266:14139–14142 (1991)). CKI also phosphorylates SV40 residues important for T2-driven replication (Cegielska et al., *Mol. Cell. Biol.* 13:120214 1211 (1993)). CKI also phosphorylates p53 (Miline et al., *J. Biol. Chem.* 270:5511–5518 (1992);Miline et al., *Oncogene* 7:1361–1369 (1992b)). In yeast, mutations in either the *S. cerevisiae* or *S. pombe* genes, HRR25 (Wnt orthologs), cause severely reduced growth when treated with DNA damaging agents (DeMaggio et al., *Proc. Nat. Acad. Sci. USA* 89:7008–7012 (1992); Dhillon et al., *EMBO J.* 13:2777–2788 (1994); Hoekstra et al., *Science* 253:1031–1034 (1991)). Expression of human CKIε (but not CKIα) rescued the slow growth phenotype of budding yeast deleted for HRR25 (Fish et al., *J. Biol. Chem.* 270:14875-83 (1995)).

Accordingly, components that could be used to phosphorylate CKI in a given sample include insulin, IL-I, and tumor necrosis factor. Substrates that are useful include, but are not limited to, CREM, glycogen synthase, and p53. In addition, as mentioned elsewhere in this application, components of the Wnt pathway are also useful as substrates, for example GSK3 and its orthologs, β-catenin and its orthologs, and Axin and its orthologs. Further, substrates capable of phosphorylating CKI could include Dvl-1 and orthologs. In addition, specific biological results that occur following a kinase reaction could also be used. This includes, but is not limited to, yeast growth assays following treatment with DNA damaging agents, rescue of the slow growth phenotype of budding yeast deleted for HRR25 (yeast CKI ortholog), induction of secondary axis for example in Xenopus, as described herein, stabilization of β-catenin or its orthologs such as Arm as described herein, and reporter of gene assays involving the Lef-1 enhancer sequence as described herein.

Antibodies

Antibodies can be used to isolate a CKI protein, and particularly a variant protein from a patient in a disease state by standard techniques such as affinity chromotography or immunoprecipitation.

The antibodies are also useful to detect the presence of CKI protein in cells or tissues to determine the pattern of expression of the CKI protein among various tissues in an organism or over the course of normal development.

The antibodies can be used to detect a protein in situ, in vitro, or in a cell lysate or supernatant in order to evaluate the abundance and pattern of expression.

The antibodies can be used to assess CKI expression in disease states, as in active stages of the disease or in an individual with a predisposition toward the disease related to the CKI function and particularly Wnt signal pathway. When a disorder is caused by an inappropriate tissue distribution, developmental expression, level of expression, the antibody can be prepared against the normal CKI protein. However, if a disorder is characterized by a specific mutation in the protein, antibodies specific for this mutant protein can be used to assay for the presence of the specific mutant protein.

The antibodies can also be used to assess normal and aberrant subcellular localization in cells in various tissues.

Antibodies can be developed against the entire protein, or against regions thereof, such as the kinase region.

The diagnostic uses can be applied, not only in genetic testing, but in monitoring a treatment modality. Accordingly, where treatment is ultimately aimed at correcting CKI expression level, antibodies directed against the CKI polypeptide can be used to monitor therapeutic efficacy.

Antibodies to CKI polypeptides, include the native proteins and variants thereof These antibodies are specific to an epitope on CKI polypeptides, and can precipitate or bind to the corresponding native protein in a cell or tissue preparation or in a cell-free extract of an in vitro expression system.

Immunogens for raising antibodies are prepared by mixing the polypeptides or fragments by native CKI genes of the present invention with adjuvants. Alternatively, polypeptides are made as fusion proteins to larger immunogenic proteins. Polypeptides are also covalently linked to other larger immunogenic proteins, such as keyhole limpet hemocyanin. Immunogens are typically administered intradermally, subcutaneously, or intramuscularly. Immunogens are administered to experimental animals such as rabbits, sheep, and mice, to generate antibodies. Optionally, the animal spleen cells are isolated and fused with myeloma cells to form hybridomas which secrete monoclonal antibodies. Such methods are well known in the art. According to another method known in the art, the CKI polynucleotide is administered directly, such as by intramuscular injection, and expressed in vivo. The expressed protein generates a variety of protein-specific immune responses, including production of antibodies, comparable to administration of the protein.

Preparations of polyclonal and monoclonal antibodies specific for CKI polypeptides are made using standard methods known in the art. The antibodies specifically bind to epitopes present in the polypeptides encoded by polynucleotides disclosed in the Sequence Listing. Typically, at least 6, 8, 10, or 12 contiguous amino acids are required to form an epitope. However, epitopes which involve non-contiguous amino acids may require more, for example at least 15, 25, or 50 amino acids.

Antibodies that specifically bind to human CKI polypeptides should provide a detection signal at least 5-, 10-, or 20-fold higher than a detection signal provided with other proteins when used in Western blots or other immunochemical assays. Preferably, antibodies that specifically bind CKI polypeptides do not detect other proteins in immunochemical assays and can immunoprecipitate CKI polypeptides from solution.

In addition to the antibodies discussed above, genetically engineered antibody derivatives are made, such as single chain antibodies.

Antibodies described above can be used in various formats to test for the presence of CKI polypeptides, such as ELISA, RIA, and immunoprecipitation formats.

METHODS OF TREATMENT

The term "CKI-mediated disorder" refers to a disease state which is caused or exacerbated by aberrant biological activity of CKI. The primary biological activity exhibited is kinase activity. This includes the ability to phosphorylate other substrates and the ability of CKI itself to be phosphorylated. The aberrant activity can be at the quantitative level or at the qualitative level (i.e., mutation).

A Wnt signal transduction-mediated disorder as it relates to the present invention is any disorder that results from CKI being inappropriately affected by and/or inappropriately affecting any component in the Wnt signal pathway. In one aspect the end result is inappropriate transcription via the Lef-1 enhancer, stabilization of β-catenin (decrease in the phosphorylated β-catenin) and thus increase in β-catenin unphosphorylated protein.

Potentially, any of the components in the pathway are relevant to the invention as long as there is involvement of the CKI component. Thus, the primary cause could be overexpression or variation in CKI that leads to increased phosphorylation of a substrate in a Wnt pathway that ultimately drives transcription. On the other hand, functional overexpression can also occur by means of a variation in the CKI protein that leads to increased rates or amounts of phosphorylation in the CKI protein, itself. Further, overexpression or mutation in a component that affects CKI leading to increased phosphorylation of CKI, for example, would also constitute a Wnt signal transduction-mediated disorder (or a CKI mediated disorder) if there is inappropriate transcription from the Lef-1 promoter.

It is thus understood that a disorder can be caused by the Wnt signal pathway where the lesion is in other than the CKI gene or protein and which, nevertheless, can be treated using the CKI nucleic acid or polypeptides described herein. Accordingly, for example, if there is a lesion in a CKI target that results in under- or over-phosphorylation, a CKI variant can be introduced to interact with the target, which itself is capable of being more or less phosphorylated or over- or under-phosphorylating. Alternatively, an antibody can be used in specific amounts to inactivate some CKI in order to compensate for the lesion in the target gene. It is understood that a target is a component that is either upstream or downstream from CKI, but with which CKI interacts.

However, it is to be understood that there may be components of the Wnt pathway that are affected by CKI which may be interrelated with other pathways such that the ultimate disorder is not caused by inappropriate transcription from the Lef-1 enhancer but from other components downstream from the affected component of the Wnt pathway. Similarly, a Wnt signal transduction-mediated disorder also encompasses a disorder that while not necessarily arising from the Lef-1 transcription originates in a Wnt component upstream from CKI in the pathway. Such components could effect CKI such that downstream components are inappropriately affected. As above, if these components participate in signaling in pathways other than the Wnt pathway, they are still indicative of a Wnt pathway-mediated disorder.

The disorder may be a biological disorder, or a medical disorder, and may be mild or severe. The diagnosis can be made based on vague or specific symptoms, and the symptoms can be local or systemic. Thus, the disorder may be part of a larger, other condition or disorder occurring in the patient. Determination of the disorder may include a physical exam and other non-invasive diagnostic procedures including, for example, radionuclide imaging, positron emission tomography, and magnetic resonance imaging.

Polynucleotides

Ribozymes and antisense polynucleotides can be constructed to inhibit CKI activity. Such molecules can be constructed from synthetic polynucleotides. Typically, the phosphoramidite method of oligonucleotide synthesis is used. See Beaucage et al., *Tet. Lett.* 22:1859–1862 (1981) and U.S. Pat. No. 4,668,777. Automated devices for synthesis are available to create oligonucleotides using this chemistry. Examples of such devices include Biosearch 8600, Models 392 and 394 by Applied Biosystems, a division of Perkin-Elmer Corp., Foster City, Calif., USA; and Expedite by Perceptive Biosystems, Framingham, Mass., USA. Synthetic RNA, phosphate analog oligonucleotides, and chemically derivatized oligonucleotides can also be produced, and can be covalently attached to other molecules.

RNA oligonucleotides can be synthesized, for example, using RNA phosphoramidites. This method can be performed on an automated synthesizer, such as Applied Biosystems, Models 392 and 394, Foster City, Calif., USA. See Applied Biosystems User Bulletin 53 and Ogilvie et al., *Pure & Applied Chem.* 59:325–330 (1987).

Phophorothioate oligonucleotides can also be synthesized for antisense construction. A sulfurizing reagent, such as tetraethylthiruam disulfide (TETD) in acetonitrile can be used to convert the internucleotide cyanoethyl phosphite to the phosphorothioate triester within 15 minutes at room temperature. TETD replaces the iodine reagent, while all other reagents used for standard phosphoramidite chemistry remain the same. Such a synthesis method can be automated using Models 392 and 394 by Applied Biosystems, for example.

Oligonucleotides of up to 200 nucleotides can be synthesized, more typically, 100 nucleotides, more typically 50 nucleotides; even more typically 30 to 40 nucleotides. Synthetic fragments can be annealed and ligated together to construct larger fragments. See, for example, Sambrook et al., supra.

Ribozymes

Trans-cleaving catalytic RNAs (ribozymes) are RNA molecules possessing endoribonuclease activity. Ribozymes are specifically designed for a particular target, and the target message must contain a specific nucleotide sequence. They are engineered to cleave any RNA species site-specifically in the background of cellular RNA. The cleavage event renders the mRNA unstable and prevents protein expression. Importantly, ribozymes can be used to inhibit expression of a gene of unknown function for the purpose of determining its function in an in vitro or in vivo context, by detecting the phenotypic effect.

Typically, the target sequence comprises sequence with substantial sequence identity to native CKI genes encoding the kinase region; in human CKI, this region is found between position 1 to 69 of the amino acid sequence. Preferably, the kinase active site at position 38 in the native human CKI is inactivated.

One commonly used ribozyme motif is the hammerhead, for which the substrate sequence requirements are minimal. Design of the hammerhead ribozyme is disclosed in Usman et al., *Current Opin. Struct. Biol.* (1996) 6:527–533. Usman also discusses the therapeutic uses of ribozymes. Ribozymes can also be prepared and used as described in Long et al., *FASEB J.* (1993) 7:25; Symons, *Ann. Rev. Biochem.* (1992) 61:641; Perrotta et al., *Biochem.* (1992) 31:16–17; Ojwang et al., *Proc. Natl. Acad. Sci. (USA)* (1992) 89:10802–10806; and U.S. Pat. No. 5,254,678. Ribozyme cleavage of HIV-I RNA is described in U.S. Pat. No. 5,144,019; methods of cleaving RNA using ribozymes is described in U.S. Pat. No. 5,116,742; and methods for increasing the specificity of ribozymes are described in U.S. Pat. No. 5,225,337 and Koizumi et al., *Nucleic Acid Res.* (1989) 17:7059–7071. Preparation and use of ribozyme fragments in a hammerhead structure are also described by Koizumi et al., *Nucleic Acids Res.* (1989) 17:7059–7071. Preparation and use of ribozyme fragments in a hairpin structure are described by Chowrira and Burke, *Nucleic Acids Res.* (1992) 20:2835. Ribozymes can also be made by rolling transcription as described in Daubendiek and Kool, *Nat. Biotechnol.* (1997) 15(3):273–277.

The hybridizing region of the ribozyme may be modified or may be prepared as a branched structure as described in Horn and Urdea, *Nucleic Acids Res.* (1989) 17:6959–67. The basic structure of the ribozymes may also be chemically altered in ways familiar to those skilled in the art, and chemically synthesized ribozymes can be administered as synthetic oligonucleotide derivatives modified by monomeric units. In a therapeutic context, liposome mediated delivery of ribozymes improves cellular uptake, as described in Birikh et al., *Eur. J. Biochem.* (1997) 245:1–16.

Using the CKI sequences of the invention and methods known in the art, ribozymes are designed to specifically bind and cut the corresponding mRNA species. Ribozymes thus provide a means to inhibit the expression of any of the CKI proteins.

A target cleavage site is selected in the target sequence, and a ribozyme is constructed based on the 5' and 3' nucleotide sequences that flank the cleavage site. Retroviral vectors are engineered to express monomeric and multimeric hammerhead ribozymes targeting the mRNA of the target coding sequence. These monomeric and multimeric ribozymes are tested in vitro for an ability to cleave the target mRNA. A cell line is stably transduced with the retroviral vectors expressing the ribozymes, and the transduction is confirmed by Northern blot analysis and reverse-transcription polymerase chain reaction (RT-PCR). The cells are screened for inactivation of the target mRNA by such indicators as reduction of expression of disease markers or reduction of the gene product of the target mRNA.

Antisense

Antisense nucleic acids are designed to specifically bind to RNA, resulting in the formation of RNA-DNA or RNA-RNA hybrids, with an arrest of DNA replication, reverse transcription or messenger RNA translation. Antisense polynucleotides based on a CKI sequence can interfere with expression of the corresponding gene. Antisense polynucleotides are typically generated within the cell by expression from antisense constructs that contain the antisense strand as the transcribed strand. Antisense polynucleotides will bind and/or interfere with the translation of CKI mRNA.

Antisense therapy for a variety of cancers is in clinical phase and has been discussed extensively in the literature. Reed reviewed antisense therapy directed at the Bcl-2 gene in tumors; gene transfer-mediated overexpression of Bcl-2 in tumor cell lines conferred resistance to many types of cancer drugs. (Reed, J. C., *N.C.I.* (1997) 89:988–990). The potential for clinical development of antisense inhibitors of ras is discussed by Cowsert, L. M., *Anti-Cancer Drug Design* (1997) 12:359–371. Additional important antisense targets include leukemia (Geurtz, A. M., *Anti-Cancer Drug Design* (1997) 12:341–358); human C-ref kinase (Monia, B. P., *Anti-Cancer Drug Design* (1997) 12:327–339); and protein kinase CKI (McGraw et al., *Anti-Cancer Drug Design* (1997) 12:315–326.

Gene Delivery Vehicle

The therapeutic polynucleotides and polypeptides of the present invention may be utilized in gene delivery vehicles. The gene delivery vehicle may be of viral or non-viral origin (see generally, Jolly, *Cancer Gene Therapy* (1994) 1:51–64; Kimura, *Human Gene Therapy* (1994) 5:845–852; Connelly, *Human Gene Therapy* (1995) 1:185–193; and Kaplitt, *Nature Genetics* (1994) 6:148–153). Gene therapy vehicles for delivery of constructs including a coding sequence of a therapeutic of the invention can be administered either locally or systemically. These constructs can utilize viral or non-viral vector approaches. Expression of such coding sequences can be induced using endogenous mammalian or heterologous promoters. Expression of the coding sequence can be either constitutive or regulated.

The present invention can employ recombinant retroviruses which are constructed to carry or express a selected nucleic acid molecule of interest. Retrovirus vectors that can be employed include those described in EP 0 415 731; WO 90/07936; WO 94/03622; WO 93/25698; WO 93/25234; U.S. Pat. No. 5,219,740; WO 93/11230; WO 93/10218; Vile and Hart, *Cancer Res.* (1993) 53:3860–3864; Vile and Hart, *Cancer Res.* (1993) 53:962–967; Ram et al., *Cancer Res.* (1993) 53:83–88; Takamiya et al., *J. Neurosci. Res.* (1992) 33:493–503; Baba et al., *J. Neurosurg.* (1993) 79:729–735; U.S. Pat. No. 4,777,127; GB Patent No. 2,200,651; and EP 0 345 242. Preferred recombinant retroviruses include those described in WO 91102805.

Packaging cell lines suitable for use with the above-described retroviral vector constructs may be readily prepared (see PCT publications WO 95/30763 and WO 92/05266), and used to create producer cell lines (also termed vector cell lines) for the production of recombinant vector particles. Within particularly preferred embodiments of the invention, packaging cell lines are made from human (such as HT1080 cells) or mink parent cell lines, thereby allowing production of recombinant retroviruses that can survive inactivation in human serum.

The present invention also employs alphavirus-based vectors that can function as gene delivery vehicles. Such vectors can be constructed from a wide variety of alphaviruses, including, for example, Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532). Representative examples of such vector systems include those described in U.S. Pat. Nos. 5,091,309; 5,217,879; and 5,185,440; and PCT Nos. WO 92/10578; WO 94/21792; WO 95/27069; WO 95/27044; and WO 95/07994.

Gene delivery vehicles of the present invention can also employ parvo virus such as adeno-associated virus (AAV) vectors. Representative examples include the AAV vectors disclosed by Srivastava in WO 93/09239, Samulski et al., *J. Virol.* (1989) 63:3822–3828; Mendelson et al., *Virol.* (1988) 166:154–165; and Flotte et al., *PNAS* (1993) 90:10613–10617.

Representative examples of adeno viral vectors include those described by Berkner, *Biotechniques* (1988) 6:616–627; Rosenfeld et al., *Science* (1991) 252:431–434; WO 93/19191; Kolls et al., *PNAS* (1994) 91:215–219; Kass-Eisler et al., *PNAS* (1993) 90:11498–11502; Guzman et al., *Circulation* (1993) 88:2838–2848; Guzman et al., *Cir. Res.* (1993) 73:1202–1207; Zabner et al., Cell (1993) 75:207–216; Li et al., *Hum. Gene Ther.* (1993) 4:403–409; Cailaud et al., *Eur. J. Neurosci.* (1993) 5:1287–1291; Vincent et al., *Nat. Genet.* (1993) 5:130–134; Jaffe et al., *Nat. Genet.* (1992) 1:372–378; and Levrero et al., *Gene* (1991) 101:195–202. Exemplary adeno viral gene therapy vectors employable in this invention also include those described in WO 94/12649, WO 93/03769; WO 93/19191; WO 94/28938; WO 95/11984 and WO 95/00655. Administration of DNA linked to killed adenovirus as described in Curiel, *Hum. Gene Ther.* (1992) 3:147–154 may be employed.

Other gene delivery vehicles and methods may be employed, including polycationic condensed DNA linked or unlinked to killed adenovirus alone, for example Curiel, *Hum. Gene Ther.* (1992) 3:147–154; ligand linked DNA, for example see Wu, *J. Biol. Chem.* (1989) 264:16985–16987; eukaryotic cell delivery vehicles cells, for example see U.S. Ser. No. 08/240,030, filed May 9, 1994, and U.S. Ser. No. 08/404,796; deposition of photo polymerized hydrogel materials; hand-held gene transfer particle gun, as described in U.S. Pat. No. 5,149,655; ionizing radiation as described in U.S. Pat. No. 5,206,152 and in WO 92/11033; nucleic charge neutralization or fusion with cell membranes. Additional approaches are described in Philip, *Mol. Cell Biol.* (1994) 14:2411–2418, and in Woffendin, *Proc. Natl. Acad Sci.* (1994) 91:1581–1585.

Naked DNA may also be employed. Exemplary naked DNA introduction methods are described in WO 90/11092 and U.S. Pat. No. 5,580,859. Uptake efficiency may be improved using biodegradable latex beads. DNA coated latex beads are efficiently transported into cells after endocytosis initiation by the beads. The method may be improved further by treatment of the beads to increase hydrophobicity and thereby facilitate disruption of the endosome and release of the DNA into the cytoplasm. Liposomes that can act as gene delivery vehicles are described in U.S. Pat. No. 5,422,120, PCT Nos. WO 95/13796, WO 94/23697, and WO 91/14445, and EP No. 0 524 968.

Further non-viral delivery suitable for use includes mechanical delivery systems such as the approach described in Woffendin et al., *Proc. Natl. Acad Sci. USA* (1994) 91(24):11581–11585. Moreover, the coding sequence and the product of expression of such can be delivered through deposition of photo polymerized hydrogel materials. Other conventional methods for gene delivery that can be used for delivery of the coding sequence include, for example, use of hand-held gene transfer particle gun, as described in U.S. Pat. No. 5,149,655; use of ionizing radiation for activating transferred gene, as described in U.S. Pat. No. 5,206,152 and PCT No. WO 92/11033.

Polypeptides

The CKI polypeptides are also useful for treating a CKI associated, and specifically a Wnt associated disorder. Accordingly, methods for treatment include administering CKI polypeptides, variants, or fragments, so as to modulate the Wnt signal transduction pathway.

Mutants can be designed that compete with endogenous CKI. Alternatively, CKI can be administered in its native form but in amounts that are sufficient to compete with a mutant CKI for substrate, compete with a mutant CKI with respect to an up-stream target molecule that interacts with endogenous CKI, or to provide levels of CKI that negatively or positively modulate the pathway. For example, a lesion in a target that over- or under-phosphorylates CKI substrate could be counteracted by using a CKI mutant that is capable of being under- or over-phosphorylated. Or a CKI downstream target that is under- or over-phosphorylated can be counteracted by using a CKI that over- or under-phosphorylates. As indicated, preferred polypeptides for treatment down-regulate the Wnt pathway by having lower or no kinase ability.

Antibodies

Antibodies are useful for inhibiting CKI function and thus modulating the Wnt CKI pathway. Antibodies can be prepared against any region of the CKI polypeptide, but preferably against the kinase domain. Antibodies can also be used to prevent binding of CKI to its substrate or prevent the binding of CKI to an up-stream molecule interacting with an activating CKI.

Pharmaceutical Compositions

Pharmaceutical compositions can comprise polypeptides, antibodies, or polynucleotides of the claimed invention. The pharmaceutical compositions will comprise a therapeutically effective amount of either polypeptides, antibodies, or polynucleotides of the claimed invention.

The term "therapeutically effective amount" as used herein refers to an amount of a therapeutic agent to treat or prevent a disorder sufficient to exhibit a detectable preventive, ameliorative, curative or other therapeutic effect. The effect may include, for example, treatment, amelioration, or prevention of any physical or biochemical condition, for example, including but not limited to hyperproliferative growth, cancer, hyperplasia, mammary cancer, mammary hyperplasia ,colon cancer, and melanoma. The precise effective amount for a subject will depend upon the subject's size and health, the nature and extent of the condition, and the therapeutics or combination of therapeutics selected for administration. Thus, it is not useful to specify an exact effective amount in advance. However, the effective amount for a given situation can be determined by routine experimentation.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients are available in *Remington's Pharmaceutical Sciences* (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

Delivery Methods

Once formulated, the polynucleotide compositions of the invention can be (1) administered directly to the subject; (2) delivered ex vivo, to cells derived from the subject; or (3) delivered in vitro for expression of recombinant proteins.

When administration is for the purpose of treatment, administration may be for either a "prophylactic" or "therapeutic" purpose. When provided prophylactically, the substance is provided in advance of any symptom. The prophylactic administration of the substance serves to prevent or attenuate any subsequent symptom. When provided therapeutically, the substance is provided at (or shortly after) the onset of a symptom. The therapeutic administration of the substance serves to attenuate any actual symptom.

Direct delivery of the compositions will generally be accomplished by injection, either subcutaneously, intraperitoneally, intravenously or intramuscularly, or delivered to the interstitial space of a tissue. The compositions can also be administered into a tumor or lesion. Other modes of administration include oral and pulmonary administration, suppositories, and transdermal applications, needles, and gene guns or hyposprays. Dosage treatment may be a single dose schedule or a multiple dose schedule.

Methods for the ex vivo delivery and reimplantation of transformed cells into a subject are known in the art and described in e.g., International Publication No. WO 93/14778. Examples of cells useful in ex vivo applications include, for example, stem cells, particularly hematopoetic, lymph cells, macrophages, dendritic cells, or tumor cells.

Generally, delivery of nucleic acids for both ex vivo and in vitro applications can be accomplished by, for example, dextran-mediated transfection, calcium phosphate precipitation, polybrene mediated transfection, protoplast fusion, electroporation, encapsulation of the polynucleotide (s) in liposomes, and direct microinjection of the DNA into nuclei, all well known in the art.

When CKI activity has been found to correlate with a proliferative disorder, such as neoplasia, dysplasia, and hyperplasia, the disorder may be amenable to treatment by administration of a therapeutic agent based on the CKI polynucleotides or polypeptides.

Preparation of antisense polynucleotides is discussed above. Neoplasias that are treated with the antisense composition include, but are not limited to, cervical cancers, melanomas, colorectal adenocarcinomas, Wilms' tumor, retinoblastoma, sarcomas, myosarcomas, lung carcinomas, leukemias, such as chronic myelogenous leukemia, promyelocytic leukemia, monocytic leukemia, and myeloid leukemia, and lymphomas, such as histiocytic lymphoma. Proliferative disorders that are treated with the therapeutic composition include disorders such as anhydric hereditary ectodermal dysplasia, congenital alveolar dysplasia, epithelial dysplasia of the cervix, fibrous dysplasia of bone, and mammary dysplasia. Hyperplasias, for example, endometrial, adrenal, breast, prostate, or thyroid hyperplasias or pseudoepitheliomatous hyperplasia of the skin, are treated with antisense therapeutic compositions. Even in disorders in which mutations in the corresponding gene are not implicated, downregulation or inhibition of gene expression can have therapeutic application. For example, decreasing CKI gene expression can help to suppress tumors in which enhanced expression of the gene is implicated.

Both the dose of the antisense composition and the means of administration are determined based on the specific qualities of the therapeutic composition, the condition, age, and weight of the patient, the progression of the disease, and other relevant factors. Administration of the therapeutic antisense agents of the invention includes local or systemic administration, including injection, oral administration, particle gun or catheterized administration, and topical administration. Preferably, the therapeutic antisense composition contains an expression construct comprising a promoter and a polynucleotide segment of at least 12, 22, 25, 30, or 35 contiguous nucleotides of the antisense strand of CKI polynucleotide. Within the expression construct, the polynucleotide segment is located downstream from the promoter, and transcription of the polynucleotide segment initiates at the promoter.

Various methods are used to administer the therapeutic composition directly to a specific site in the body. For example, a small metastatic lesion is located and the therapeutic composition injected several times in several different locations within the body of tumor. Alternatively, arteries which serve a tumor are identified, and the therapeutic composition injected into such an artery, in order to deliver the composition directly into the tumor. A tumor that has a necrotic center is aspirated and the composition injected directly into the now empty center of the tumor. The antisense composition is directly administered to the surface of the tumor, for example, by topical application of the composition. X-ray imaging is used to assist in certain of the above delivery methods.

Receptor-mediated targeted delivery of therapeutic compositions containing an antisense polynucleotide, subgenomic polynucleotides, or antibodies to specific tissues is also used. Receptor-mediated DNA delivery techniques are described in, for example, Findeis et al., Trends in Biotechnol. (1993) 11:202–205; Chiou et al., (1994) Gene Therapeutics: Methods And Applications Of Direct Gene Transfer (J. A. Wolff, ed.); Wu & Wu, J. Biol. Chem. (1988) 263:621–24; Wu et al., J. Biol. Chem. (1994) 269:542–46; Zenke et al., Proc. Natl. Acad. Sci. (USA) (1990) 87:3655–59; Wu et al., J. Biol. Chem. (1991) 266:338–42. Preferably, receptor-mediated targeted delivery of therapeutic compositions containing antibodies of the invention is used to deliver the antibodies to specific tissue.

Therapeutic compositions containing antisense subgenomic polynucleotides are administered in a range of about 100 mg to about 200 mg of DNA for local administration in a gene therapy protocol. Concentration ranges of about 500 mg to about 50 mg, about 1 µg to about 2 µg, about 5 µg to about 500 µg, and about 20 µg to about 100 µg of DNA can also be used during a gene therapy protocol. Factors such as method of action and efficacy of transformation and expression are considerations which will affect the dosage required for ultimate efficacy of the antisense subgenomic polynucleotides. Where greater expression is desired over a larger area of tissue, larger amounts of EST antisense subgenomic polynucleotides or the same amounts readministered in a successive protocol of administrations, or several administrations to different adjacent or close tissue portions of, for example, a tumor site, may be required to effect a positive therapeutic outcome. In all cases, routine experimentation in clinical trials will determine specific ranges for optimal therapeutic effect. A more complete description of gene therapy vectors, especially retroviral vectors, is contained in U.S. Ser. No. 08/869,309, which is expressly incorporated herein, and in the section below.

EXPERIMENTAL

EXAMPLE 1

Isolation of a Gene Modulating Wnt Signal Transduction

Genes involved in axis-formation in Xenopus, were isolated using an expression cloning strategy described previously (Lemaire et al., Cell 81:85–94 (1995)). Synthetic mRNA from pools of clones were injected into the ventral-vegetal blastomeres of 4-cell stage embryos. These were scored for a secondary axis at the tailbud stage. A mouse embryo E14 cDNA library was constructed in a pCS2+ vector. The library was pooled to 25 clones per pool and mRNA was synthesized in vitro from an SP6 promoter and injected into 4-cell stage embryos.

Several clones induced secondary axes. One of these encoded a mouse CKI, 98.9% identical to human CKIε. It is also 85% identical to a rat CKIδ isoform. It encodes 416 amino acids, a core kinase domain of 285 amino acids and a C-terminal tail of 123 amino acids. The kinase domain is 53–98% identical to the kinase domains of other CKI family members and is most closely related to the δ isoform. When 80 pg of this CKIε mRNA was injected into embryos, a complete double axis was formed. This result shows that a casein kinase protein functions as an axis inducing factor.

A number of factors downstream of the Wnt signal have been shown to induce a secondary axis in Xenopus, (e.g. a dominant negative, GSK3) (He et al., Nature 374:617–622 (1995); Pierce et al., Development 121:755–65 (1995)), Xenopus Disheveled (Xdsh) (Sokol et al., Development 121:1637–47 (1995)), β-catenin (Kamovsky et al., Proc. Natl. Acad Sci. USA 92:4522–4526 (1995); McCrea et al., J. Cell. Biol. 123:477–484 (1993)), lef-1 (Behrens et al., Nature 382:638–42 (1996); Molenaar et al., Cell 86:391–399 (1996)).

The fact that CKI induced a secondary axis suggested that CKI could modulate Wnt signaling by interacting with the Wnt pathway downstream of the Wnt signal, with for example, GSK3, Dv1-1, β-catenin, or Lef-1.

EXAMPLE 2

Interaction of CKI with the Wnt (Wg) Pathway

Drosophila Schneider cell lines were derived that stably express CKIε in the presence or absence of Drosophila Sgg (GSK3) protein. CKIε and sgg (GSK3) gene expression were controlled by a metallothionein promoter which is induced by copper. In cells expressing CKIε, Arm (β-catenin) protein level is significantly higher than background. In the cells expressing CKIε and Sgg (GSK3), Arm (β-catenin) protein level is reduced. This suggests that CKI is regulated in mammals by GSK3 (Sgg) so that it cannot induce β-catenin (Arm) accumulation.

EXAMPLE 3
Interaction of CKI with Mammalian Wnt Pathway

The effect of CKI on Lef-1 dependent transcription in Cos mammalian cells was examined. A luciferase reporter gene driven by multiple copies of the Lef-I enhancer sequence was used. When only Wnt-I or lef-I or CKIε was transfected with the reporter construct, luciferase activity was induced only 2 to 3 fold (FIG. 1A). When Lef-1 was cotransfected with either Wnt-1 or CKIε, luciferase activity was induced 30 or 12 fold respectively. Wnt-I and CKI without lef-I did not induce the transcription (FIG. 1A). This result shows that CKI positively affects the Wnt pathway downstream from Wnt signaling, obviating the need for Wnt, allowing stabilization of β-catenin, which then forms a stable complex with Lef-1, transactivating transcription.

EXAMPLE 4
Construction of a CKI Variant With the Capability of Modulating the Wnt Signal Pathway A kinase-inactive CKIε construct was made in which lysine 38 in the kinase domain was mutated to arginine. It was transiently transfected into Cos cells and its activity was tested using substrate casein protein. The variant showed no detectable kinase activity.

When CKIε mRNA was injected into ventralized Xenopus embryos, it rescued embryonic dorsal structure. In contrast, variant mRNA injection could not rescue dorsal development. Furthermore, when the variant was co-transfected with CKIε into Cos cells, Lef-1-dependent luciferase activity was inhibited. Similarly, when the variant gene was co-transfected with Wnt-1, it blocked the Wnt signal transduction in a dose-dependent manner. Thus, the variant interferes with Wnt signaling, acting as a dominant negative.

The variant also inhibited the effect of Dv1-1 on luciferase activity. This shows that wild-type CKI is required to facilitate Dvl-1 function (i.e. to inhibit GSK3, and ultimately, to stabilize β-catenin).

EXAMPLE 5
Relationship of CKI and GSK3

The results of the experiment described in Example 2 suggested that CKI is upstream of GSK3 because overexpression of Sgg (GSK3) inhibited Arm (GSK3) stabilization by CKI. This suggestion arises in view of the fact that GSK3 acts directly on β-catenin. Accordingly, GSK3 was over-expressed to test the effect on CKI using the luciferase assay. Over-expression of GSK3 inhibited the effect of CKI in promoting transcription.

Figure 2A:
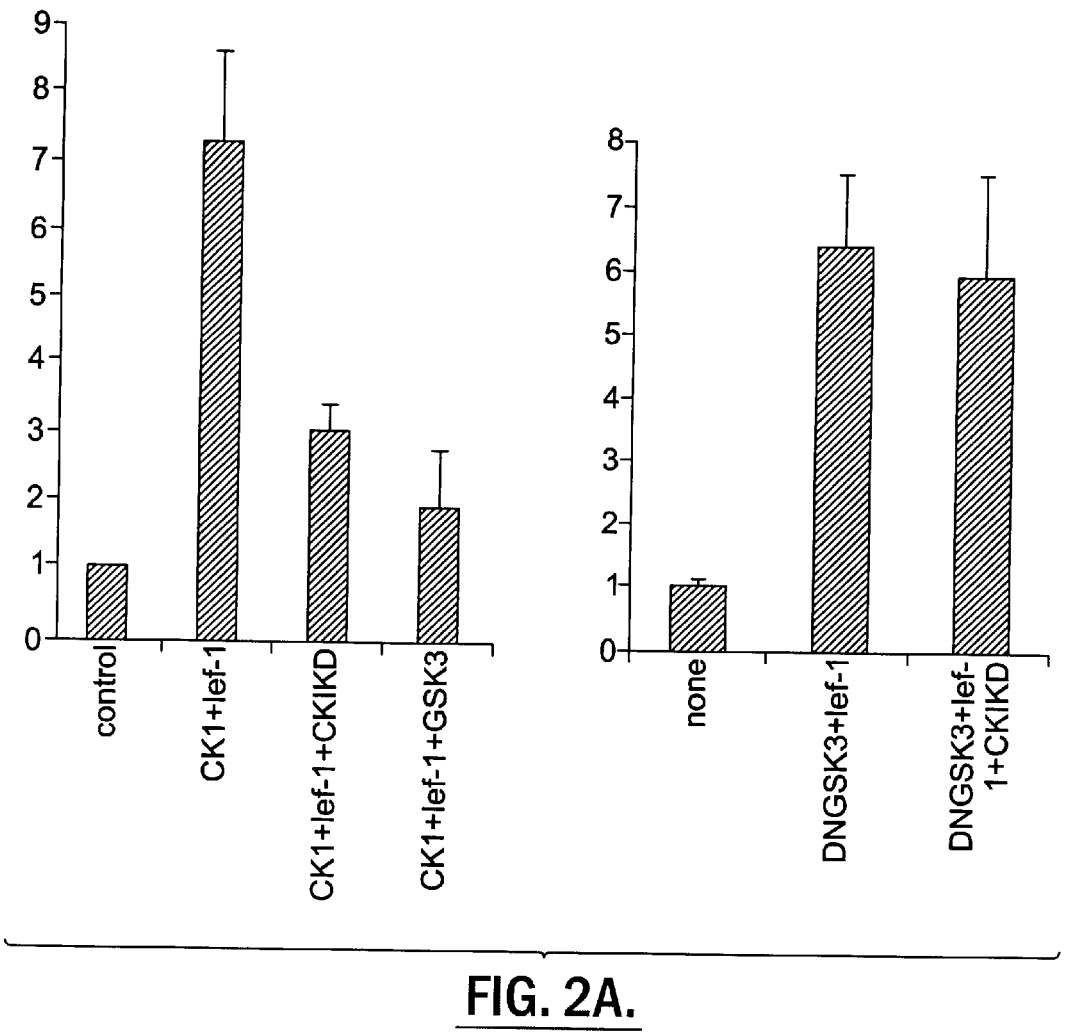

The luciferase assay was also used to test the effect of the kinase-dead CKI variant on GSK3 function. Co-transfection of the variant with the dominant negative GSK3 and Lef-1 did not reduce the signal transduced by the dominant negative GSK3 (FIG. 2A). This suggests that CKI is either upstream of or parallel to GSK3 in the Wnt pathway.

When CKIε was cotransfected with GSK3, GSK3 could be detected in immune complexes with CKIε (FIG. 2A). These data indicate that CKIε interacts with GSK3.

In vitro, either purified CKIε protein or immunoprecipitated CKIε phosphorylated purified GSK3 protein as well as immunoprecipitated GSK3 protein (FIG. 2B).

The fact that CKIε interacts with GSK3 or kinase-dead GSK3 (DNGSK3) as well as Axin in vivo suggests that CKIε may work directly on GSK3 or Axin by phosphorylating GSK3 or Axin. It was shown that β-catenin/APC complex interacts with GSK3 in a kinase-dependent manner (i.e. the complex does not interact with kinase-dead GSK3). Phosphorylation of APC by GSK3 was required for the interaction of β-catenin and APC. It appears that Axin also interacts with β-catenin and GSK3 simultaneously.

EXAMPLE 6
Interaction of CKI With Axin

When CKIε and Axin were both expressed in Cos cells, they were found in the same immunoprecipitation complex. When Axin RNA was coinjected with CKIε RNA into Xenopus embryos, the number of embryos with double-axes was reduced 50% compared to embryos injected with CKIε RNA alone.

Isolation of Mouse CKI and Construction of Plasmids

An E14 mouse embryo library was made of oligo(dT) primed cDNA in a pCS2+vector (EcoRI/XbaI). Minipreps of DNA of pools of 25–50 plasmids were prepared and linearized with NotI. Synthetic capped mRNA was prepared using mMessage mMachine kit (Ambion #1340) with a reaction time of 2–4 hours. RNA pools were injected into a ventralvegetal blastmere at the 4–8 cell stage of Xenopus embryos. Embryos were scored for double axes at 24 hours and 2–3 days. A positive pool was selected by retransfecting the pooled DNA into bacteria and 96 single clones were screened in order to obtain a positive clone.

CKIε-HA, huGSK3myc and mouse Dvl-I (gluglu tagged) were PCR-cloned into pCS2+ at EcoRI and XbaI sites. All tags were at the C-terminal end. CKIKD-HA was mutated by PCR using a 5' primer containing a point mutation Lys-Arg.

Northern Blot and In Situ Hybridization

Mouse multiple tissue and mouse embryo Northern blots were from CLONTECH (#7762–1 and #7763–1). CKIε cDNA was isolated from the plasmid by EcoRI and XbaI digestion. CKIε cDNA and GAPDH cDNA were labeled using the Rediprime DNA labeling system (Amersham #RPNI633/1634). Northern blots were done using ExpressHyb described in CLONTECH #8015-1/-2. The blots were first hybridized to the CKIε probe and then stripped and hybridized to GAPDH probe.

Stable Drosophila Schneider Cells

CKIε was PCR-cloned into a vector pRmHa-3 containing a copper-inducible promoter (metallothionine). It was co-transfected with pMKK3 containing the neo-gene (G418-resistant gene) into Drosophila Schneider cells. G418 was used for selection of a stable cell line. In addition, stable cell lines containing combinations of CKIε+wt sgg, CKIε+Actsgg, CKIKD, CKIKD+DN Sgg were made. Actsgg is a mutant containing a mutation of Ser9 to Ala. To detect stabilized Arm, cells were plated 16 hours before the copper induction and lysed three hours after the copper induction. Western blots were performed with anti-Arm mAb 7A12.

Luciferase Reporter Assay

Luciferase reporter plasmid contains multiple Lef-I enhancer sites upstream of the fos basal promoter. Various DNA plasmids encoding Wnt-1, CKIε, Dvl-1, GSK3 etc. were co-transfected with a luciferase reporter plasmid and a SV40 β-galactosidase plasmid into 24-well Cos cell culture. For each well, 0.5 μg total DNA was in a ratio of 0.08 μg:016 μg:0.02 μg for signaling molecules:luciferase: β-gal. SV40 β-gal construct was used as an internal transfection control, since β-gal activity is independent of the Wnt-1 signaling molecules. Transfection was done using LT1 (5 μl/μg DNA) (Panvera Co. # MIR23 10). Each sample was transfected in triplex repeats to obtain a statistical value. After 24 hours, cells were washed once with PBS and lysed in 50 μl/well lysis buffer supplied with the luciferase assay kit (Promega cat# EI500). 10 μl of each sample was aliquoted into two sets of tubes, one set for the luciferase assay and another for β-gal chemiluminescent reporter assay (Galacto-Light, TROPIX Inc. #BL100G). The result of the luciferase assay was divided by the corresponding β-gal activity, and then averaged.

EXAMPLE 7
Importance of the C-terminus of CKIε in the Wnt pathway

There are seven mammalian CKI isoforms (α, β, γ$_{1-3}$, δ and ε). All these isoforms contain a conserved serine-threonine kinase domain and various amino terminal and carboxyl terminal domains. CKIε and CKIδ the most closely related isoforms have a longer carboxy terminus compared to the other isoforms. CKIε and CKIδ isoforms activate the Wnt pathway where as this is but this is not the case with CKIα. The activation of the Wnt pathway was analyzed by induction of ectopic axis in Xenopus embryos and the Lef-1 reporter gene assay. C-terminally truncated CKIε fails to activate the Wnt pathway, although this mutant CKIε has kinase activity. These data suggests that the CKI effect on the Wnt pathway is specific to the ε and δ isoforms, and the carboxyl terminal domain is required for mediating response.

Interaction of CKI with Axin When Axin was expressed in 293 cells, endogenous CKIε was found in the Axin immune-complex. C-terminally truncated CKIε bound less Axin when both molecules were co-expressed in 293 cells. These data inducates that Axin associates with primarily with the C-terminal domain of CKIε.

Interaction of CKI with Dvl

When Dvl3 was expressed in 293 cells, endogenous CKIε was found in the Dvl3 immune-complex. Thus CKIε and Dvl3 are in a common complex. CKIε may be involved in early events in the Wnt pathway.

Possible Mechanism of CKI Function in the Wnt Pathway

The possible mechanism of CKIε in the Wnt pathway is to regulate protein stability. The Drosophila homologue of CKIε, double-time was shown to regulate the stability of its kinase substrates (Kioss et al., Cell (1998) 94(1):97–107.). Overexpression of CKIε causes stabilization of cytosolic pool of β-catenin protein. The stabilization of the cytosolic β-catenin results in activation of the Wnt pathway. β-catenin is known to be phosphorylated by GSK-3 and binds to β-TRCP (beta-transducin repeat containing protein). So that it is ready to be degraded through the ubiquitin-proteasome pathway (Aberle et al., EMBO J. (1997)16(13):3797–804; Orford et al., J. Biol Chem. (1997) 272(40):24735–8.). CKIε phosphorylates β-catenin in vitro. However in contrast to phosphorylation of β-catenin by GSK-3, preliminary data suggests that XKIε phosphorylates β-catenin by a mechanism that may inhibit the degradation of β-catenin through the ubiquitination pathway. Phosphorylation of β-catenin by CKIε may inhibit the phosphorylation by GSK-3 and/or its binding to β-TRCP. Axin helps GSK-3 phosphorylate β-catenin. It has been shown that Axin is destabilized upon stimulation of Wnt pathway (Yamamoto et al., J. Biol Chem. (1999) 274(16):10681-4; Willert et al., Genes Dev. (1999) 13(14):1768–73.). CKIε phosphorylates Axin, and this phosphorylation may accelerate the degradation process of Axin.

The other possible mechanism by which CKIε regulates the Wnt pathway is through Dishevelled, since CKIε binds and phosphorylates Dishevelled in vivo. Dishevelled activates the Wnt pathway and is known to be phosphorylated by Wnt stimulation (Yanagawa et al., Genes Dev. (1995) 9(9):1087–97.; Lee et al., J. Biol Chem.(1999) 274(30):21464–70.). Phosphorylation by CKIε may enhance Dishevelled function in the Wnt pathway.

Lef-1 Reporter Gene Assay

Lef-1 reporter assays were carried out as done as described in Sakanaka et al. (1998) Proc Natl Acad Sci USA. 95:3020–3. For example, 293 cells were seeded at 2×105 cells/well in 12-well culture plates. Cells were transfected with 0.2 μg of the luciferase reporter gene, 0.02 μg of Lef-1, 0.03 μg of pTK-β-gal as an internal control, the indicated amount of CKIε, Axin or Wnt-1 cDNA, and pcDNA3.1 vector to a total amount of 0.4 μg of plasmids. Transfection was performed by Lipofectamine (Lifetechnologies Inc. #18324012). Luciferase and β-gal activities were measured 48 h after transfection. Relative light units (RLU) were measured with a luminometer (Analytical Luminescence Laboratory, Monolight 2010).

Immunological Procedures

Cells were washed with PBS and lysed in buffer (20 mM Tris.HCl, pH 7.5/1 mM EDTA/0.1% Triton X-100/0.15 mM NaCl/1 mM phenylmethylsulfonyl fluoride/10 μg/ml each of aprotinin and leupeptin). For immunoprecipitation, cell lysates were incubated with various antibodies for 4 hours at 4° C., then added Dynabeads M-450 Sheep anti-Mouse IgG (Dynal Inc. #110.01). Enhance chemiluminescence reagents (Amersham Pharmacia Biotech) were used for detection of the immunoblots.

EXAMPLE 8
Therapeutic Potential Of CKIε Inhibition

In order to study the therapeutic potential of CKIε inhibition and specifically the use of antisense polynucleotides to inhibit CKIε antisense polynucleotides were designed which specifically bind to CKIε. The result is formation of RNA-DNA or RNA-RNA hybrids, with an arrest of DNA replication, reverse transcription of messenger RNA translation and interference with the expression of CKIε. Examples of CKIε antisense polynucleotides used are
GCGGCAGAAGTTGAGGTATGTTGAG (SEQ ID NO:5) and
CGCCGTCTTCAACTCCATACAACTC (SEQ ID NO:6).

The Wnt pathway has been shown to be involved in many oncogenic processes and inhibition of CKIε is proposed to inhibit the wnt pathway and thus treat hyperpoliferative disorders. In order to evaluate the efficacy of CKIε inhibition in blocking Wnt signaling, the ability of antisense polynucleotides against CKIε to inhibit both Wnt and β-catenin-induced activation of gene expression was measured.

Figure 4A:
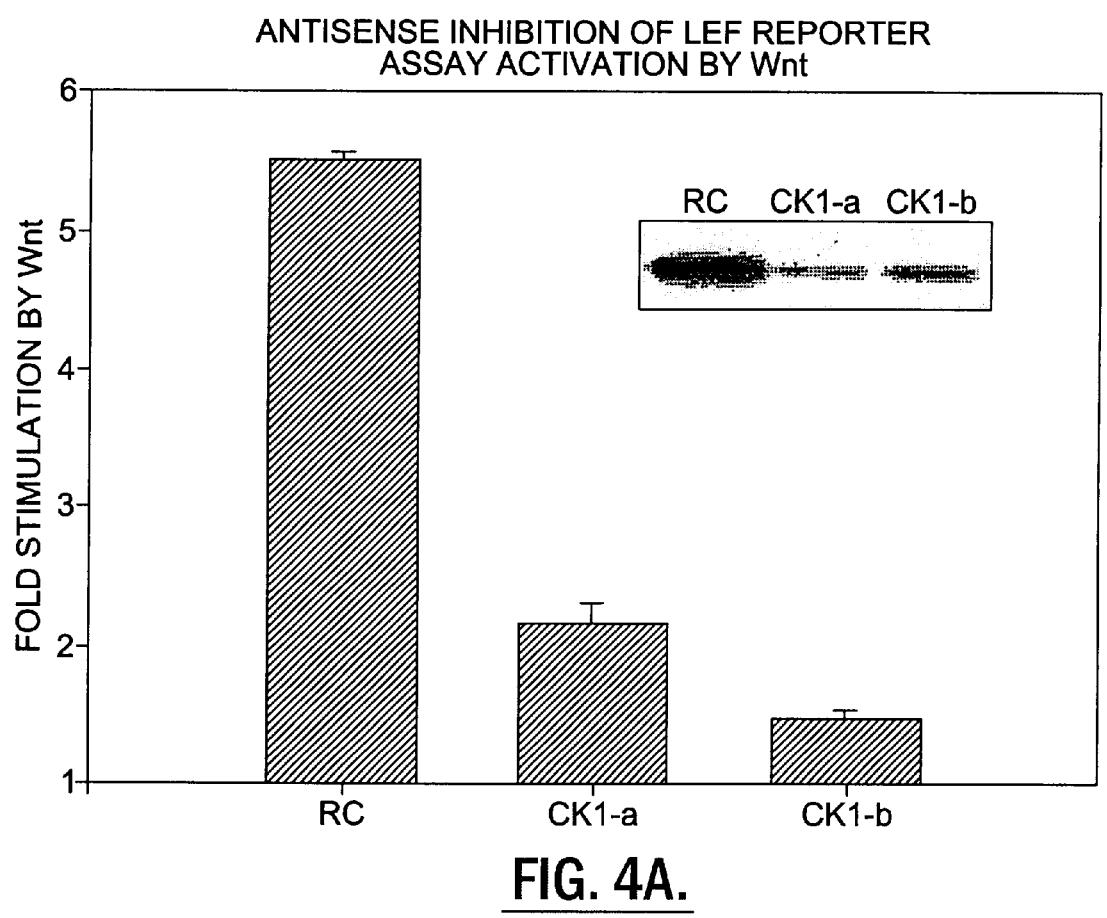
FIGS. 4A–C Lef-1 reporter gene activity induced by Wnt (A), Dvl-3 (B), or mutant β-catenin (C) is inhibited by CKIε antisense polynucleotides (CKI-a and CKI-b), but not by the reverse sequence control (RC). 293 cells were plated at a density of $1.5*10^5$ cells per 12-well dish 16 hours prior to transfection 6 ul 0.5 mM cationic lipitoid and 2 ul 100 uM polynucleotide in 50 ul opti-MEM (Life Technologies) was mixed together and added dropwise to cells in 1 ml of fresh media. After 24 hours cells, cells were washed with opti-MEM and transfected with luciferase reporter plasmids (0.02 mg lef-1, 0.2 lef-1 reporter, 0.03 mg renilla luciferase) control using lipofectamine (Life Technologies). Cells were assayed for luciferase activity 48 hours after transfection of antisense polynucleotides.
Figure 4C:
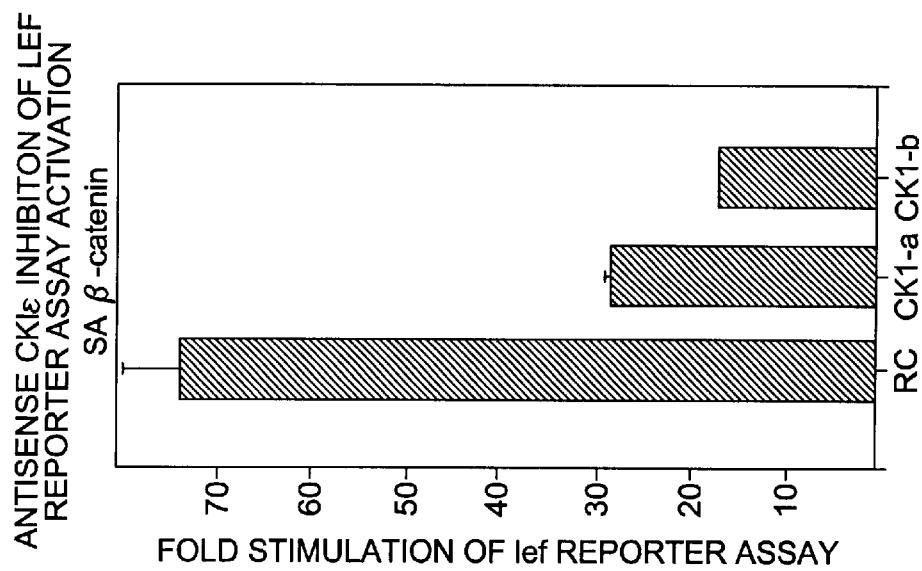
Figure 4B:
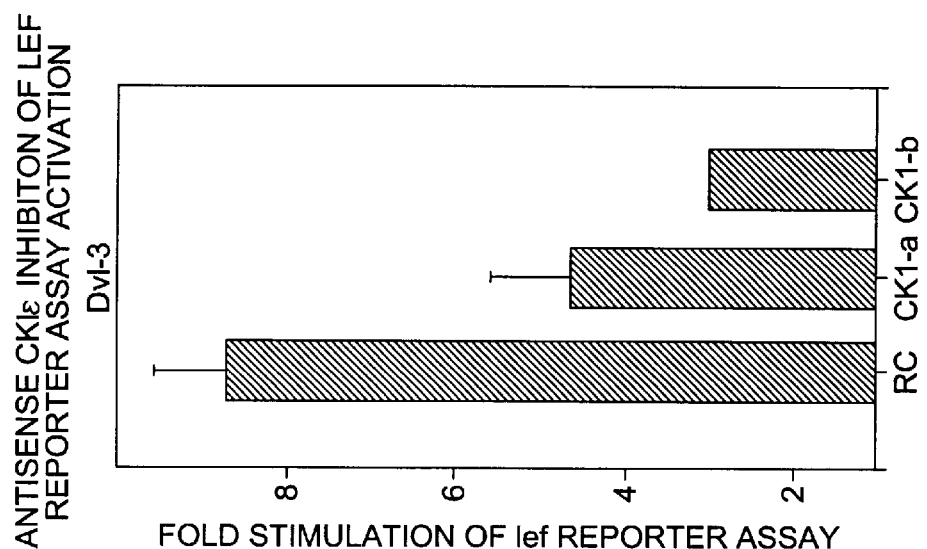
Figure 5:
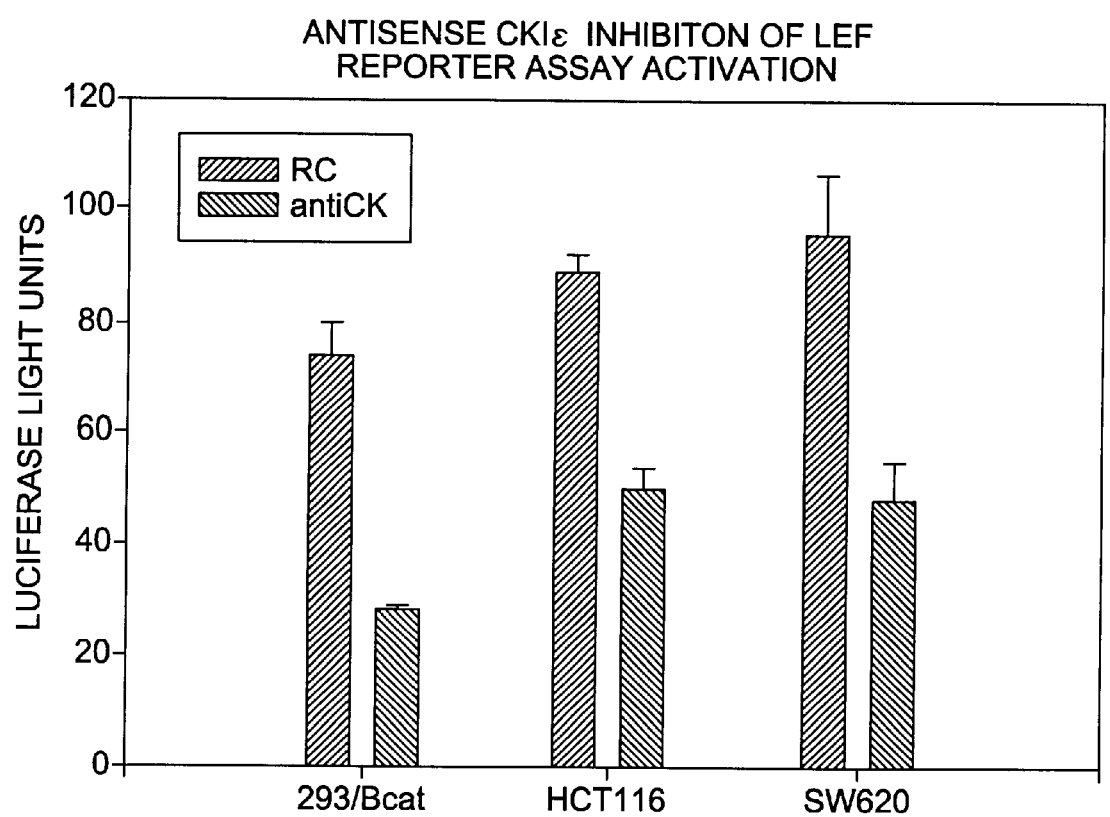
FIG. 5. Lef-1 reporter gene activity is inhibited by CKIε antisense polynucleotides in cells overexpressing β-catenin (293), and in colon cancer cells with mutation in β-catenin (HCT116) or APC (SW620). Cells were plated 24 hours prior to treatment at a density of $1.5*10^5$ for 293, $6*104$ HCT116, and $2.25*10^5$ for SW620. Cells were transfeted as described in FIG. 5 and assayed for luciferase activity 48 hours after transfection with antisense polynucleotides (anti-CK) or reverse control (RC).

One method for measuring activation of gene expression by the Wnt pathway is to use the Lef-1 reporter gene assay. Antisense polynucleotides were transfected into cells by using cationic peptoid reagents followed by transfection with Lef-1, Lef-1 reporter, and Wnt-1 plasmids using lipofectamine (Life Technologies). Lef-1 reporter gene activity was measured using the Dual-Luciferase Reporter Assay System (Promega) according to the manufacturers specifications. When expressed in 293 cells, Wnt-1 was observed to stimulate the expression of Lef-1 reporter gene transcription 4–6 fold over vector transfected cells. Prior treatment of 293 cells with CKIε antisense to reduce endogenous CKIε protein level resulted in the inhibition of Lef-1 reporter gene activity induced by Wnt (FIG. 4). In colon cancer cells with mutations in β-catenin or APC which lead to the stabilization of β-catenin, the Lef-1 reporter gene transcription was inhibited by CKIε antisense (FIG. 5).

A second method for measuring the activity of the Wnt pathway is to look at the regulation of transcription of specific genes. A central feature of this pathway is the Wnt-mediated stabilization of cytosolic β-catenin. To mimic Wnt-stimulation, β-catenin plasmids were transfected into 293 cells, and after 24 hours mRNA was isolated using Rneasy and Oligotex mRNA Kits (Qiagen) and gene expression was measured using DNA microarray technology. A set of genes was determined to be upregulated relative to untreated cells. Similarly, colon cancer cell lines with muta tions in β-catenin and APC were transfected with CKIε antisense, RNA was isolated 48 hours later, and gene expression was analyzed using microarrays. A subset of the genes that were upregulated by β-catenin stabilization were shown to be downregulated by CKIε antisense.

Using these two assays for measuring the activity of the Wnt pathway, antisense inhibition of CKIε was shown to be effective in reversing the upregulation of genes by the Wnt pathway and β-catenin stabilization. These genes are postulated to play a role in hyperpoliferative disorders.

Other modifications and embodiments of the invention will come to mind in one skilled in the art to which this invention pertains having the benefit of the teachings presented herein. Therefore, it is to be understood that the invention is not to be limited to the specific embodiments disclosed. Although specific terms are employed, they are used in generic and descriptive sense only and not for purposes of limitation, and that modifications and embodiments are intended to be included within the scope of the appended claims.

What is claimed is:

1. An isolated nucleic acid molecule comprising a nucleotide sequence encoding a polypeptide variant of the casein kinase I epsilon (CKIε) polypeptide having the sequence set forth in SEQ ID NO:1, wherein said polypeptide variant has an amino acid sequence that differs from the sequence set forth in SEQ ID NO:1 by having a mutation within the kinase region defined by amino acid residues 1–69 of SEQ ID NO:1, wherein said mutation is an amino acid substitution that results in under-phosphorylation of the polypeptide variant by a phosphorylating molecule with respect to phosphorylation of said CKIε polypeptide by said phosphorylating molecule, or wherein said mutation results in under-phosphorylation of a CKIε substrate by said polypeptide variant with respect to phosphorylation of said CKIε substrate by said CKIε polypeptide.

2. The isolated nucleic acid molecule of claim 1, wherein said CKIε polypeptide is encoded by the nucleotide sequence set forth in SEQ ID NO:2.

3. The isolated nucleic acid molecule of claim 1, wherein said amino acid substitution occurs at the amino acid residue homologous to residue 38 of SEQ ID NO:1, whereby arginine is substituted for lysine.

4. An isolated nucleic acid molecule comprising a nucleotide sequence encoding a kinase-inactive caseine kinase I epsilon (CKIε) polypeptide, wherein said polypeptide has the sequence set forth in SEQ ID NO:1 with arginine substituted for lysine at amino acid residue 38 of SEQ ID NO:1.

5. The nucleic acid molecule of claim 4, wherein said nucleotide sequence encoding said kinase-inactive CKIε polypeptide is the sequence set forth in SEQ ID NO:2 with a single point mutation in nucleotides 130–132 of SEQ ID NO:2, whereby said single point mutation results in said substitution of arginine for said lysine.

* * * * *

UNITED STATES PATENT AND TRADEMARK OFFICE
CERTIFICATE OF CORRECTION

PATENT NO.    : 6,512,102 B1
DATED         : January 28, 2003
INVENTOR(S)   : Xu et al.

It is certified that error appears in the above-identified patent and that said Letters Patent is hereby corrected as shown below:

Column 20,
Line 33, in the equation, "10C" should read -- $10C_i$ -- so the equation reads as such:
-- $T_m = 81 + 16.6(\log 10C_i) + 0.4[\%G+C] - 0.6(\%\text{formamide}) - 600/n - 1.5(\%\text{mismatch})$ --

Signed and Sealed this

Fifteenth Day of July, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,512,102 B1
DATED : January 28, 2003
INVENTOR(S) : Xu et al.

It is certified that error appears in the above-identified patent and that said Letters Patent is hereby corrected as shown below:

<u>Column 20,</u>
Line 33, in the equation, "10C" should read -- $10C_i$ -- so the equation reads as such:
-- $T_m = 81 + 16.6(\log 10C_i) + 0.4[\%G+C] - 0.6(\%\text{formamide}) - 600/n - 1.5(\%\text{mismatch})$ --

<u>Column 46,</u>
Line 13, delete the phrase "homologous to residue".

This certificate supersedes Certificate of Correction issued July 15, 2003.

Signed and Sealed this

Twelfth Day of August, 2003

JAMES E. ROGAN
*Director of the United States Patent and Trademark Office*

SEQUENCE LISTING

```
<160> NUMBER OF SEQ ID NOS: 6

<210> SEQ ID NO 1
<211> LENGTH: 416
<212> TYPE: PRT
<213> ORGANISM: Mus Casein Kinase I epsilon

<400> SEQUENCE: 1

Met Glu Leu Arg Val Gly Asn Lys Tyr Arg Leu Gly Arg Lys Ile Gly
 1               5                  10                  15

Ser Gly Ser Phe Gly Asp Ile Tyr Leu Gly Ala Asn Ile Ala Ser Gly
             20                  25                  30

Glu Glu Val Ala Ile Lys Leu Glu Cys Val Lys Thr Lys His Pro Gln
         35                  40                  45

Leu His Ile Glu Ser Lys Phe Tyr Lys Met Met Gln Gly Gly Val Gly
     50                  55                  60

Ile Pro Ser Ile Lys Trp Cys Gly Ala Glu Gly Asp Tyr Asn Val Met
65                  70                  75                  80

Val Met Glu Leu Leu Gly Pro Ser Leu Glu Asp Leu Phe Asn Phe Cys
                 85                  90                  95

Ser Arg Lys Phe Ser Leu Lys Thr Val Leu Leu Leu Ala Asp Gln Met
            100                 105                 110

Ile Ser Arg Ile Glu Tyr Ile His Ser Lys Asn Phe Ile His Arg Asp
        115                 120                 125

Val Lys Pro Asp Asn Phe Leu Met Gly Leu Gly Lys Lys Gly Asn Leu
    130                 135                 140

Val Tyr Ile Ile Asp Phe Gly Leu Ala Lys Lys Tyr Arg Asp Ala Arg
145                 150                 155                 160

Thr His Gln His Ile Pro Tyr Arg Glu Asn Lys Asn Leu Thr Gly Thr
                165                 170                 175

Ala Arg Tyr Ala Ser Ile Asn Thr His Leu Gly Ile Glu Gln Ser Arg
            180                 185                 190

Arg Asp Asp Leu Glu Ser Leu Gly Tyr Val Leu Met Tyr Phe Asn Leu
        195                 200                 205

Gly Ser Leu Pro Trp Gln Gly Leu Lys Ala Ala Thr Lys Arg Gln Lys
    210                 215                 220

Tyr Glu Arg Ile Ser Glu Lys Lys Met Ser Thr Pro Ile Glu Val Leu
225                 230                 235                 240

Cys Lys Gly Tyr Pro Ser Glu Phe Ser Thr Tyr Leu Asn Phe Cys Arg
                245                 250                 255

Ser Leu Arg Phe Asp Asp Lys Pro Asp Tyr Ser Tyr Leu Arg Gln Leu
            260                 265                 270

Phe Arg Asn Leu Phe His Arg Gln Gly Phe Ser Tyr Asp Tyr Val Phe
        275                 280                 285
```

```
Asp Trp Asn Met Leu Lys Phe Gly Ala Ala Arg Asn Pro Glu Asp Val
    290                 295                 300

Asp Arg Glu Arg Arg Glu His Glu Arg Glu Arg Met Gly Gln Leu
305                 310                 315                 320

Arg Gly Ser Ala Thr Arg Ala Leu Pro Pro Gly Pro Pro Thr Gly Ala
                325                 330                 335

Thr Ala Asn Arg Leu Arg Ser Ala Ala Glu Pro Val Ala Ser Thr Pro
                340                 345                 350

Ala Ser Arg Ile Gln Gln Thr Gly Asn Thr Ser Pro Arg Ala Ile Ser
        355                 360                 365

Arg Ala Asp Arg Glu Arg Lys Val Ser Met Arg Leu His Arg Gly Ala
        370                 375                 380

Pro Ala Asn Val Ser Ser Asp Leu Thr Gly Arg Gln Glu Val Ser
385                 390                 395                 400

Arg Leu Ala Ala Ser Gln Thr Ser Val Pro Phe Asp His Leu Gly Lys
                405                 410                 415

<210> SEQ ID NO 2
<211> LENGTH: 1353
<212> TYPE: DNA
<213> ORGANISM: Mus Casein Kinase I epsilon
<220> FEATURE:
<221> NAME/KEY: CDS
<222> LOCATION: (19)...(1266)

<400> SEQUENCE: 2
attcgggcac gaggaagc atg gag ttg cgt gtg gga aat aag tat cgc ctg          51
                    Met Glu Leu Arg Val Gly Asn Lys Tyr Arg Leu
                      1               5                  10 ggc cga aag atc ggc agt ggc tcc ttt gga gac atc tac ctg ggt gcc          99
Gly Arg Lys Ile Gly Ser Gly Ser Phe Gly Asp Ile Tyr Leu Gly Ala
             15                  20                  25 aac att gcc tct ggt gag gaa gta gcc atc aag ctc gaa tgt gtg aag         147
Asn Ile Ala Ser Gly Glu Glu Val Ala Ile Lys Leu Glu Cys Val Lys
         30                  35                  40 acg aaa cat ccc cag ctc cac atc gag agc aag ttc tac aag atg atg         195
Thr Lys His Pro Gln Leu His Ile Glu Ser Lys Phe Tyr Lys Met Met
     45                  50                  55 cag ggc gga gtg ggg atc ccg tcc atc aag tgg tgc ggg gct gag gga         243
Gln Gly Gly Val Gly Ile Pro Ser Ile Lys Trp Cys Gly Ala Glu Gly
 60                  65                  70                  75 gac tat aac gtg atg gtc atg gag ctg ctg ggg ccc agc ctg gag gac         291
Asp Tyr Asn Val Met Val Met Glu Leu Leu Gly Pro Ser Leu Glu Asp
                 80                  85                  90 ctc ttc aac ttc tgt tcc cgg aag ttc agc ctc aag acg gtg ctg ttg         339
Leu Phe Asn Phe Cys Ser Arg Lys Phe Ser Leu Lys Thr Val Leu Leu
             95                 100                 105 ctg gcc gac cag atg atc agc cgc atc gag tac ata cac tcc aag aac         387
Leu Ala Asp Gln Met Ile Ser Arg Ile Glu Tyr Ile His Ser Lys Asn
        110                 115                 120 ttc atc cac cgg gat gtg aag ccc gac aac ttc ctc atg ggc ctg ggg         435
Phe Ile His Arg Asp Val Lys Pro Asp Asn Phe Leu Met Gly Leu Gly
    125                 130                 135 aag aaa ggc aac ctg gtg tac atc att gac ttc ggc ctg gcc aag aag         483
Lys Lys Gly Asn Leu Val Tyr Ile Ile Asp Phe Gly Leu Ala Lys Lys
140                 145                 150                 155 tac cgc gat gcc cgc aca cac cag cat att ccc tac cgg gaa aac aag         531
Tyr Arg Asp Ala Arg Thr His Gln His Ile Pro Tyr Arg Glu Asn Lys
                160                 165                 170
```

```
aac ctg act ggc act gcc cgc tat gcc tct atc aac acc cac ctg ggc    579
Asn Leu Thr Gly Thr Ala Arg Tyr Ala Ser Ile Asn Thr His Leu Gly
            175                 180                 185 att gag caa agc cgt cga gat gac cta gag agc ttg ggc tat gtg ctc    627
Ile Glu Gln Ser Arg Arg Asp Asp Leu Glu Ser Leu Gly Tyr Val Leu
            190                 195                 200 atg tac ttc aac ctg ggc tcc ctg ccc tgg cag ggc ctc aaa gca gcc    675
Met Tyr Phe Asn Leu Gly Ser Leu Pro Trp Gln Gly Leu Lys Ala Ala
205                 210                 215 acc aag cgt cag aag tac gag cgg att agc gag aag aag atg tca acg    723
Thr Lys Arg Gln Lys Tyr Glu Arg Ile Ser Glu Lys Lys Met Ser Thr
220                 225                 230                 235 cca atc gag gtc ctc tgc aaa ggc tac ccc tcc gag ttc tca aca tac    771
Pro Ile Glu Val Leu Cys Lys Gly Tyr Pro Ser Glu Phe Ser Thr Tyr
                240                 245                 250 ctc aac ttc tgc cgc tcc ctg cgg ttc gat gat aag cct gac tac tcc    819
Leu Asn Phe Cys Arg Ser Leu Arg Phe Asp Asp Lys Pro Asp Tyr Ser
                255                 260                 265 tac ctg cgc cag ctc ttc cga aat ctc ttt cac cgg cag ggt ttc tcc    867
Tyr Leu Arg Gln Leu Phe Arg Asn Leu Phe His Arg Gln Gly Phe Ser
                270                 275                 280 tac gac tac gtc ttc gac tgg aac atg ctc aaa ttc ggt gca gcc cgg    915
Tyr Asp Tyr Val Phe Asp Trp Asn Met Leu Lys Phe Gly Ala Ala Arg
285                 290                 295 aat ccc gag gat gta gac cgg gaa aga cgg gag cac gaa cgg gaa gag    963
Asn Pro Glu Asp Val Asp Arg Glu Arg Arg Glu His Glu Arg Glu Glu
300                 305                 310                 315 agg atg ggg cag ttg cga ggg tcc gcg acc aga gcc ctg ccc cct ggc   1011
Arg Met Gly Gln Leu Arg Gly Ser Ala Thr Arg Ala Leu Pro Pro Gly
                320                 325                 330 cca cct aca ggg gct acc gcc aac cga ctc cga agt gca gcc gag cct   1059
Pro Pro Thr Gly Ala Thr Ala Asn Arg Leu Arg Ser Ala Ala Glu Pro
                335                 340                 345 gtg gct tcc act cca gcc tcc cgc atc caa caa act ggc aat act tct   1107
Val Ala Ser Thr Pro Ala Ser Arg Ile Gln Gln Thr Gly Asn Thr Ser
                350                 355                 360 ccc aga gcg atc tca cgg gcc gac cga gag agg aag gtg agc atg aga   1155
Pro Arg Ala Ile Ser Arg Ala Asp Arg Glu Arg Lys Val Ser Met Arg
365                 370                 375 ctc cac aga ggt gcc cct gcc aat gtc tcc tcc tca gac ctc act ggg   1203
Leu His Arg Gly Ala Pro Ala Asn Val Ser Ser Ser Asp Leu Thr Gly
380                 385                 390                 395 cgg caa gag gtc tcc cgg ctt gca gcc tca cag aca agc gtg cca ttt   1251
Arg Gln Glu Val Ser Arg Leu Ala Ala Ser Gln Thr Ser Val Pro Phe
                400                 405                 410 gac cat ctt ggg aaa tgaggagagc gaccacagac cagtgtttgc ttagtgtctt   1306
Asp His Leu Gly Lys
            415 cactgcattt tctttaaaaa aaaaaaaaaa aaactcgagc tctaga                1353

<210> SEQ ID NO 3
<211> LENGTH: 1353
<212> TYPE: DNA
<213> ORGANISM: Mus Casein Kinase I epsilon
<220> FEATURE:
<221> NAME/KEY: misc_feature
<222> LOCATION: (1)...(1353)
<223> OTHER INFORMATION: antisense strand 3' to 5'

<400> SEQUENCE: 3
```

-continued

```
taagcccgtg ctccttcgta cctcaacgca cacccttttat tcatagcgga cccggctttc      60
tagccgtcac cgaggaaacc tctgtagatg acccacggt tgtaacggag accactcctt      120
catcggtagt tcgagcttac acacttctgc tttgtagggg tcgaggtgta gctctcgttc     180
aagatgttct actacgtccc gcctcacccc tagggcaggt agttcaccac gccccgactc     240
cctctgatat tgcactacca gtacctcgac gaccccgggt cggacctcct ggagaagttg     300
aagacaaggg ccttcaagtc ggagttctgc cacgacaacg accggctggt ctactagtcg     360
gcgtagctca tgtatgtgag gttcttgaag taggtggccc tacacttcgg gctgttgaag     420
gagtacccgg acccctctt tccgttggac cacatgtagt aactgaagcc ggaccggttc      480
ttcatggcgc tacgggcgtg tgtggtcgta taagggatgg ccctttttgtt cttggactga    540 ccgtgacggg cgatacggag atagttgtgg gtggacccgt aactcgtttc ggcagctcta     600
ctggatctct cgaacccgat acacgagtac atgaagttgg acccgaggga cgggaccgtc     660
ccggagtttc gtcggtggtt cgcagtcttc atgctcgcct aatcgctctt cttctacagt     720
tgcggttagc tccaggagac gtttccgatg gggaggctca agagttgtat ggagttgaag     780
acggcgaggg acgccaagct actattcgga ctgatgagga tggacgcggt cgagaaggct     840
ttagagaaag tggccgtccc aaagaggatg ctgatgcaga agctgacctt gtacgagttt     900
aagccacgtc gggccttagg gctcctacat ctggccttt ctgccctcgt gcttgccctt     960
ctctcctacc ccgtcaacgc tcccaggcgc tggtctcggg acgggggacc gggtggatgt    1020
ccccgatggc ggttggctga ggcttcacgt cggctcggac accgaaggtg aggtcggagg    1080
gcgtaggttg tttgaccgtt atgaagaggg tctcgctaga gtgcccggct ggctctctcc    1140
ttccactcgt actctgaggt gtctccacgg ggacggttac agaggaggag tctggagtga    1200
cccgccgttc tccagagggc cgaacgtcgg agtgtctgtt cgcacggtaa actggtagaa    1260
ccctttactc ctctcgctgg tgtctggtca caaacgaatc acagaagtga cgtaaaagaa    1320 atttttttttt tttttttttg agctcggaga tct                                1353
```

```
<210> SEQ ID NO 4
<211> LENGTH: 16
<212> TYPE: PRT
<213> ORGANISM: Artificial Sequence
<220> FEATURE:
<223> OTHER INFORMATION: a C-terminal extension for purification process

<400> SEQUENCE: 4

Ser Tyr Pro Tyr Asp Val Pro Asp Tyr Ala Ser Leu Gly Gly Pro Ser
  1               5                  10                  15

<210> SEQ ID NO 5
<211> LENGTH: 25
<212> TYPE: DNA
<213> ORGANISM: Artificial Sequence
<220> FEATURE:
<223> OTHER INFORMATION: antisense sequence to CKI-epsilon

<400> SEQUENCE: 5
gcggcagaag ttgaggtatg ttgag                                             25

<210> SEQ ID NO 6
<211> LENGTH: 25
<212> TYPE: DNA
<213> ORGANISM: Artificial Sequence
```

-continued

```
<220> FEATURE:
<223> OTHER INFORMATION: antisense sequence to CKI-epsilon

<400> SEQUENCE: 6
cgccgtcttc aactccatac aactc                                               25
```